(12) United States Patent
Asrar et al.

(10) Patent No.: US 7,771,749 B2
(45) Date of Patent: Aug. 10, 2010

(54) LIGNIN-BASED MICROPARTICLES FOR THE CONTROLLED RELEASE OF AGRICULTURAL ACTIVES

(75) Inventors: Jawed Asrar, Chesterfield, MO (US); Yiwei Ding, Ballwin, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 10/191,703

(22) Filed: Jul. 9, 2002

(65) Prior Publication Data

US 2003/0013612 A1    Jan. 16, 2003

Related U.S. Application Data

(60) Provisional application No. 60/304,554, filed on Jul. 11, 2001.

(51) Int. Cl.
*A61K 9/14* (2006.01)
*A61K 31/70* (2006.01)

(52) U.S. Cl. .................. 424/484; 424/489; 514/22

(58) Field of Classification Search ............ 504/359; 514/963, 353, 383, 448, 63, 22; 424/484, 424/489
See application file for complete search history.

(56) References Cited

U.S. PATENT DOCUMENTS

| | | | |
|---|---|---|---|
| 3,726,850 A * | 4/1973 | Detroit | 530/501 |
| 3,813,236 A | 5/1974 | Allan | 71/94 |
| 3,929,453 A * | 12/1975 | Dimitri et al | 424/362 |
| 3,992,532 A | 11/1976 | Dimitri | 424/213 |
| RE29,238 E | 5/1977 | Dimitri et al. | 71/101 |
| 4,184,866 A * | 1/1980 | Dellicolli et al. | 71/68 |
| 4,244,728 A | 1/1981 | DelliColli et al. | 71/65 |
| 4,244,729 A | 1/1981 | DelliColli et al. | 71/65 |
| 4,381,194 A | 4/1983 | DelliColli et al. | 71/65 |
| 4,612,051 A | 9/1986 | Miller, Jr. et al. | 106/30 |
| 4,624,694 A | 11/1986 | DelliColli | 71/77 |
| 4,751,247 A | 6/1988 | Dilling et al. | 514/777 |
| 4,752,319 A | 6/1988 | DelliColli | 71/77 |
| 4,797,157 A | 1/1989 | Dilling et al. | 106/20 |
| 4,846,986 A | 7/1989 | Trivett | 252/49.5 |
| 4,911,736 A | 3/1990 | Huang et al. | 44/51 |
| 4,960,814 A | 10/1990 | Wu et al. | 524/312 |
| 5,525,595 A | 6/1996 | Takagaki et al. | 514/27 |
| 5,552,149 A | 9/1996 | Lebo, Jr. et al. | 424/408 |
| 5,994,331 A | 11/1999 | Erdelen et al. | 514/137 |
| 6,077,860 A | 6/2000 | Meunier et al. | 514/341 |
| 6,114,362 A | 9/2000 | Dutzmann et al. | 514/341 |

FOREIGN PATENT DOCUMENTS

| | | |
|---|---|---|
| EP | 0381290 A2 | 8/1990 |
| EP | 1038441 A2 | 9/2000 |
| EP | 1038442 A2 | 9/2000 |
| EP | 1 404 176 B1 | 2/2006 |
| MX | 242784 | 10/2002 |
| PH | 12004500044 | 12/2007 |
| WO | WO 92/19102 | 11/1992 |
| WO | WO-99/00013 | * 1/1999 |
| WO | WO 99/00013 | 1/1999 |
| WO | WO 99/44581 | 9/1999 |
| WO | WO 00/27200 | 5/2000 |
| WO | 03005816 | 1/2003 |

OTHER PUBLICATIONS

Ferraz et al, Controlled release of 2,4-D from Granule Matrix Formulation Based on Six Lignins, J. Agric. Food Chem., 1997, 45, 1001-1005.*

Fernandez-Perez et al, Controlled release of imidacloprid from a Lignin Matrix: Water Release Kinetics and Soil Mobility Study, J. Agric. Food Chem., 1998, 46, 3828-3834.*

Wilkins et al, Management of the rice tungro virus vector Nephotettix virescens (Homoptera: Cicadellidae) with controlled-release formulations of carbofuran, J. of Economic Entomology, 1984, vol. 77, No. 2, pp. 495-499. ABS.*

Pereira et al, Mathematical modeling of controlled release kinetics of herbicides in a dynamic-water-bath system, Applied Biochemistry and Biotechnology—Part A Enzyme Engineering and Biotechnology—Part A Enzyme Engineering and Biotechnology, 2001, 91-937.-(563-574), 9 references. ABS.*

Zhao et al., Controlled release of a herbicide from matrix granules based on solvent-fractioned Organosolv Lignins ,J. of Agricultural and Food Chemistry, 2000, 48(8), pp. 3651-3661.*

(Continued)

*Primary Examiner*—Alton N Pryor
(74) *Attorney, Agent, or Firm*—Nelson Mullins Riley & Scarborough, LLP

(57) ABSTRACT

A method of producing lignin-based matrix microparticles for the controlled release of an agricultural active includes forming an emulsion of an organic solution in an aqueous solution, wherein the organic solution contains a lignin derivative and an agricultural active in a volatile organic solvent and the aqueous solution contains an emulsifier; and removing the organic solvent, thereby producing microparticles having a matrix comprising the lignin derivative within which the agricultural active is distributed. Small, spherical lignin-based matrix microparticles that release an agricultural active at a controlled rate are described, as are plants and plant propagation materials that are treated with such microparticles.

33 Claims, 12 Drawing Sheets

OTHER PUBLICATIONS

Ni et al, Alcell lignin solubility in ethanol-water mixtures, J. of Applied Polymer Science, 57 (12), pp. 1441-1446.*

Controlled-Release Delivery Systems for Pesticides, Herbert B. Scher, Marcel Dekker, Inc., New York, Chapter 4 Entitled Controlled Release of Pesticides from Microparticles, Darren J. Park et al. pp. 89-136 (1999).

Controlled-Release Delivery Systems for Pesticides, Herbert B. Scher, Marcel Dekker, Inc., New York, Chapter 5 Entitled Dispersible Microparticles, Kelly L. Smith, pp. 137-149 (1999).

Journal of Agricultural and Food Chemistry, vol. 46, No. 9, Controlled Release of Imidacloprid from a Lignin Matrix: Water Release Kinetics and Soil Mobility Study, Manuel Fernandez-Perez et al, pp. 3828-3834 (1998).

Pesticide Science, vol. 55, Use of Bentonite and Humic Acid as Modifying Agents in Alginate-Based Controlled-Release Formulations of Imidacloprid, E. Gonzalez-Pradas, et al, pp. 546-552 (1999).

International Search Report dated Nov. 15, 2002 for International Application No. PCT/US02/21722.

Abstract XP-002218555, "Lignin granule delivery systems," by R.M. Wilkins, published by *Abstr. Pap. Am. Chem. Soc.* (220 Meet., Pt. 1, AGRO076, 2000).

Abstract XP-002218554, "Controlled Release of Imidacloprid from Lignin Matrix Formulations," by Allan et al, published in *Proceed. Int'l. Symp. Control. Rel. Bioact. Mater.,* 25(1998), pp. 659-660.

Article identified as XP-008009586, "Controlled Release Granules, with Emphasis on Lignin-Based Methods," by Richard M. Wilkins, published in *Controlled Release Delivery Systems for Pesticides*, Marcel Dekker Inc.: New York, US. 1999, pp. 195-222.

Office Action Paper No. 5, mailed Mar. 30, 2007 from the Intellectual Property Philippines for Application No. 12004500044.

Response to Office Action Paper No. 5 dated Jul. 6, 2007 as filed with the Intellectual Property Philippines for Application No. 12004500044.

Office Action Paper No. 11, mailed Aug. 10, 2007 from the Intellectual Property Philippines for Application No. 12004500044.

Response to Office Action Paper No. 11 dated Oct. 8, 2007 as filed with the Intellectual Property Philippines for Application No. 12004500044.

Office Action dated Jun. 29, 2009 from the Canadian Intellectual Property Office for Application No. 2,452,509.

Response dated Dec. 22, 2009 to the Office Action dated Jun. 29, 2009 from the Canadian Intellectual Property Office for Application No. 2,452,509.

Translation dated May 25, 2006 of Office Action from the Mexican Intellectual Property Office for Application No. PA/a/2004/000236.

Response to the Office Action from the Mexican Intellectual Property Office for PA/a/2004/000236.

Office Action dated Feb. 19, 2004 from European Patent Office for Application No. 02748113.4-2117.

Response to Office Action dated Feb. 19, 2004 from European Patent Office for Application No. 02748113.4-2117.

Office Action dated Jun. 28, 2004 from European Patent Office for Application No. 02748113.4-2117.

Response to Office Action dated Jun. 28, 2004 from European Patent Office for Application No. 02748113.4-2117.

Office Action dated Nov. 23, 2004 from European Patent Office for Application No. 02748113.4-2117.

Response to Office Action dated Nov. 23, 2004 from European Patent Office for Application No. 02748113.4-2117.

Office Action dated Feb. 1, 2005 from European Patent Office for Application No. 02748113.4-2117.

Response to Office Action dated Feb. 1, 2005 from European Patent Office for Application No. 02748113.4-2117.

* cited by examiner

LIGNIN-BASED MICROPARTICLES FOR THE CONTROLLED RELEASE OF AGRICULTURAL ACTIVES

The present application claims the benefit of U.S. Provisional Application Ser. No. 60/304,554 filed Jul. 11, 2001, which is incorporated herein by reference thereto.

BACKGROUND OF THE INVENTION (1) Field of the Invention:

The present invention relates to matrix microparticles for the controlled release of agricultural actives, and more particularly to methods of producing lignin-based matrix microparticles for the controlled release of agricultural actives.

(2) Description of the Related Art:

Pesticides, herbicides, plant growth regulating compounds and other related compounds are widely used to protect plants from diseases and pests and ultimately to increase crop yield or value. In addition to the potential benefits that such compounds promise, however, many of these materials are toxic to humans and other animals. Some can be harmful to the plants they are intended to protect. Thus, the consequences of unanticipated contact with such compounds over a long term or at high concentrations is undesirable. Moreover, because such compounds are complex molecules, most of which must be chemically synthesized, they are often expensive to produce, and can be chemically fragile. Therefore, in addition to the potential environmental harm that can be caused by leaching, blowing and other movement of the materials away from the area of initial application, some of these compounds are quickly degraded by ultraviolet (UV) light. These losses reduce the effectiveness of the compound and increase the amount that must be applied in order to provide a desired benefit.

One strategy for managing the safety and effectiveness of many of these biologically active compounds has been to provide them as controlled release formulations. Such formulations provide the active within a structure which limits the rate of transfer of the active into the surrounding environment and minimizes the movement of the active away from the site of application. General information on controlled release formulations for agricultural actives can be found in: *Controlled-Release Delivery Systems for Pesticides*, H. B. Scher, Ed., Marcel Dekker, Inc., NY (1999), *Microencapsulation*, Benita, S., (Ed.), Marcel Dekker, Inc., New York (1996), *Controlled Delivery of Crop-Protection Agents*, Wilkins, R. M., (Ed.), Taylor & Francis Ltd., London (1990), and Fernandez-Perez, M. et al., *J. Agric. Food Chem.,* 46:3828 (1998), among others.

Common forms of controlled release formulations include microcapsules, microparticles and granules. Generally, microcapsules are considered to be particles of 1-100 microns in size that are composed of a distinct wall and a core that contains the active. Microparticles is a term that is generally used to describe matrix particles of 1-100 microns in size that have the active more or less uniformly distributed or dispersed within the matrix. Granules are matrix particles that are 0.2-2 mm in size with the active more or less uniformly distributed or dispersed throughout the matrix.

Each of these controlled release forms has advantages and disadvantages. For example, microcapsules that are formed by coating small solid particles of an active with a barrier material, often a polymer, are often of uneven shape and have uneven coating thickness over the surface of the particle—some even having exposed surfaces of the active. Accordingly, it is often difficult to assure predictable and even release of the active from such coated particles. Some coated particles permit high levels of the active at the surface and this can increase the exposure of handlers to the active and can result in rapid loss of the active upon application. These same disadvantages are also present in granules that have been produced by absorption of the active onto a carrier material.

Microcapsules having regular spherical shape and uniform walls can be formed by in situ polymerization of a polymeric barrier wall at the surface of droplets in emulsions. A common example is the reaction of a polyamine in one liquid phase with a polyisocyanate in another phase to form a polyurea wall surrounding a core containing an active. See, e.g., U.S. Pat. No. 5,525,595 to Seitz et al. However, the reactants that are suitable for such formulations are somewhat limited, and this can limit the types of active with which this technique can be successfully used. Furthermore, the production of such microcapsules having consistent properties requires careful control and expensive reactants.

Uniformly spherical particles, which demonstrate predictable and regular release rates, can also be provided by the formation of matrix microparticles. General information on the production of matrix microparticles can be found in *Controlled release of pesticides from microparticles*, Park, D. J., et al., Ch. 4, pp. 89-137, and in *Dispersible microparticles*, Smith, K. L., Ch. 5, pp. 137-149, both in *Controlled-Release Delivery Systems for Pesticides*, Scher, H. B., Ed., Marcel Dekker, Inc., New York (1999).

It is generally known that the release of a molecule, such as an agricultural active, from a matrix microparticle depends upon, among other things, the size and geometry of the particle and the compatibility between the active and the matrix material. Moreover, the compatibility between the active and the matrix material can also affect whether it is possible to successfully produce a useful matrix microparticle from a given active and a given matrix material. For example, if there is insufficient compatibility between the active and the matrix material, a majority of the active can be excluded from the matrix microparticle during the formation process. Such a product is characterized by a high concentration of the active present as crystals, or on the surface of the microparticles, and results in uncontrolled release of the active into the environment. A microparticle formulation having high levels of the active outside the particles, or on the surface of the particles, is usually found to have a high readily extractable active (REA) value.

Because of the often complex chemistries of modern agricultural actives, it has not been possible to predict a priori which combinations of active and matrix material can be expected to yield effective matrix microparticles having low REA values. For example, recently introduced chloronicotinyls have been shown to be useful as insecticides (See., e.g., U.S. Pat. Nos. 5,994,331, 6,077,860, 6,114,362), but their successful inclusion in controlled release forms that are capable of sustained release over periods longer than a few days has been difficult. See, e.g., Gonzalez-Pradas, E., *Pestic. Sci.,* 55:546-552 (1999), and Fernandez-Perez, M., *J. Agric. Food Chem.,* 46(9):3828-3834 (1998).

Because controlled release formulations that are designed for agricultural uses necessarily must be of a lower cost than, for example, medical applications, it is important to provide such formulations that can be produced economically and efficiently. Moreover, because such formulations are usually applied directly to plants or into the soil, it is important that the particles be biodegradable, so as not to persist in the environment.

Due to its wide availability and properties as a UV protectant, lignin has been used as a carrier or adjuvant for actives in agricultural compositions. For example, Dilling et al., in U.S. Pat. Nos. 4,751,247 and 4,797,157, describe the use of amine salts of ligonulfonates as a sequestrant in pesticide compositions. The use of alkali lignin as a pesticide dispersant was taught in U.S. Pat. Nos. 3,726,850 and 3,992,532. U.S. Pat. No. 3,813,236 described the covalent bonding of a pesticide to a lignin substrate, and U.S. Pat. No. 3,929,453, reissued as Re. No. 29,238, taught a slow release composite produced by co-precipitation of an alkali lignin or the removal of a common solvent from a lignin-pesticide mixture.

Other lignin-based sustained release formulations were described in U.S. Pat. Nos. 4,184,866, 4,244,728 and 4,244,729, each of which teaches the cross-linking of lignin with epichlorohydrin or formaldehyde.

In U.S. Pat. No. 4,381,194, the adsorption of a herbicide or fungicide onto particles of a water-insoluble alkali lignin and a surfactant, where the lignin had a mean particle size of from 0.5 to 5 microns in diameter. In U.S. Pat. Nos. 4,624,694 and 4,752,319, DelliColli described the use of a similar lignin slurry, except without the herbicide or fungicide, as a method of crop seed treatment to provide an increase in emergence of seedlings.

Lignosulfonates, in combination with a protein such as a high bloom gelatin, were reported in U.S. Pat. No. 5,552,149 to be useful for the formation of microcapsules that were resistant to UV degradation.

Other lignin derivatives, such as for example, lignin acetate, have been reported to be useful for applications such as acting as a binder in water-based printing ink compositions. (See, e.g., U.S. Pat. No. 4,612,051).

Accordingly, therefore, it would be useful to provide controlled release microparticles and formulations for agricultural actives that could be produced from readily available, biodegradable materials that would have a low environmental impact. It would also be useful if such microparticles would stabilize the active against UV degradation. Furthermore, it would be useful if such microparticles could be made to be sufficiently small so that they could be used effectively as components in a seed coating, but still capable of maintaining the release of the active over a period of time of several weeks, or months.

SUMMARY OF THE INVENTION

Briefly, therefore the present invention is directed to a novel method of producing lignin-based matrix microparticles for the controlled release of an agricultural active, the method comprising the steps of:

forming an emulsion of an organic solution in an aqueous solution, wherein the organic solution contains a lignin derivative and an agricultural active in a volatile organic solvent and the aqueous solution contains an emulsifier; and removing the organic solvent, thereby producing microparticles having a matrix comprising the lignin derivative within which the agricultural active is distributed.

The present invention is also directed to a novel formulation for the controlled release of an agricultural active, the formulation comprising predominantly spherical matrix microparticles having a matrix of a lignin derivative within which an agricultural active is distributed.

The present invention is also directed to a novel method of treating a plant or its propagation material, the method comprising contacting the plant or its propagation material with the formulation described just above.

The present invention is also directed to a novel treated plant or its propagation material comprising a plant or its propagation material that has been contacted with the formulation described above.

Among the several advantages found to be achieved by the present invention, therefore, may be noted the provision of controlled release microparticles for agricultural actives that can be produced from readily available, biodegradable materials that have a low environmental impact, and the provision of such materials and formulations that can stabilize the active against UV degradation, and the provision of such microparticles that are sufficiently small so that they can be used effectively as components in a seed coating, but still are capable of maintaining the release of the active over a period of time of several weeks, or months.

DETAILED DESCRIPTION OF THE PREFERRED EMBODIMENTS

Figure 1A:
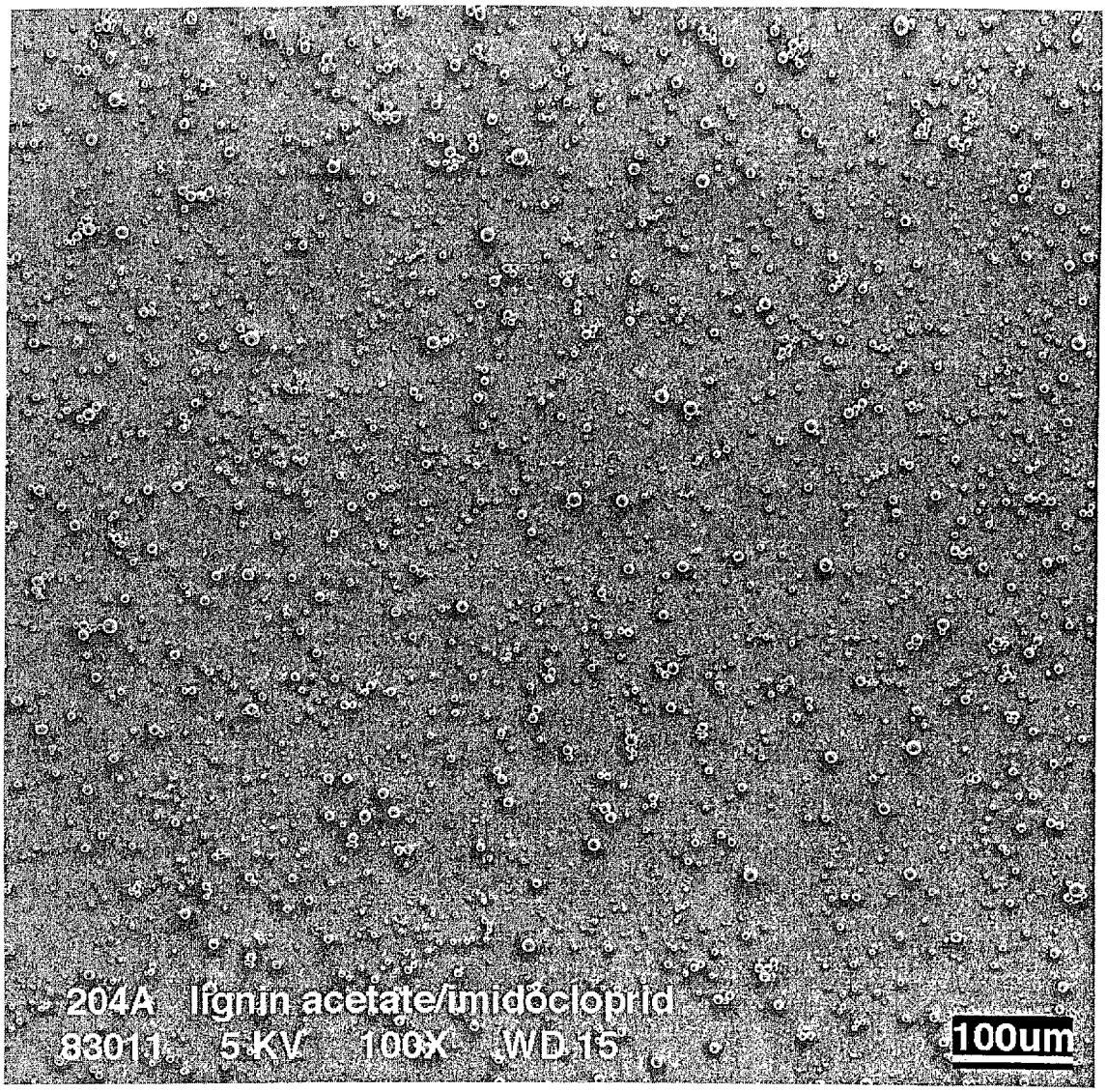
FIG. 1 shows electron micrographs of lignin-based matrix microparticles of the present invention which contain imidacloprid taken at magnifications of 100×(1(a)), 500×(1(b)), 1000×(1(c)), and 2000×(1(d))

In accordance with the present invention, it has been discovered that lignin-based matrix microparticles for the controlled release of an agricultural active can be prepared by forming an aqueous solution that includes an emulsion stabilizer, forming an organic solution by dissolving a lignin derivative and an agricultural active in a volatile organic solvent, and combining the aqueous solution and the organic solution in a manner that results in the formation of an emulsion of the organic solution in the aqueous solution. The organic solvent can then be removed from the emulsion, with the resulting production of microparticles having a matrix comprising the lignin derivative within which the agricultural active is distributed.

The subject lignin-based matrix microparticles are easy to produce with conventional equipment and techniques and can be designed to provide long-term release of the agricultural active that is enclosed within the matrix. Release half-lives of over about 2000 hours have been reported, even for microparticles of less than about 20 microns in average size. This unexpectedly advantageous combination of properties permits the subject microparticles to be used efficiently in seed treatments that require protection of long duration, such as, for example, the treatment of winter wheat seed, which benefits from significant residual activity at even three or four months after planting.

The term "matrix", as used herein, means a continuous solid phase of one or more lignin-based binder compounds throughout which is distributed as a discontinuous phase one or more of the subject agricultural actives. Optionally, a filler and/or other components can also be present in the matrix.

The subject method of production captures the active within the microparticle with a high level of efficiency, but avoids high levels of easily lost, or readily extractable active (REA).

The lignin-based microparticles of the present invention can be produced by providing an organic solution that contains a lignin derivative and an agricultural active in a volatile organic solvent. The organic solution is intermixed with an aqueous solution to form an emulsion. It has been found to be easier to form a stable emulsion having the preferred droplet, or particle, size, when a suitable emulsifier is present when the two solutions are intermixed. It is preferred that the emulsion be an oil-in-water type emulsion in which the organic solution forms the discontinuous phase and the aqueous solution forms the continuous phase. After the emulsion has been formed, the organic solvent is removed, thereby producing microparticles having a matrix comprising the lignin derivative within which the agricultural active is distributed.

The preferred emulsifier is one that is compatible with the agricultural active and one in whose presence an oil-in-water emulsion is more stable that an emulsion in which the emulsifier is absent. When it is said that the preferred emulsifier is compatible with the agricultural active, it is meant that the emulsifier is dispersible in, or preferably, soluble in the active.

Useful emulsifiers include anionic, cationic, nonionic and amphoteric emulsifiers.

Examples of useful anionic emulsifiers include soap-alkali metal salts of fatty acids, such as sodium stearate; salts of tall oil acids; alkyl naphthalene sulfonates and condensates, such as Lomar D (Henkel); fatty alcohol monoesters of sulfonic acids, such as Conco Sulfate M; linear alkyl benzene sulfonates, such as sodium n-dodecylbenzenesulfonate; lignin sulfonates; alkane and α-olefin sulfonates, such as Bio-Terge AS-40 (Stepan); sulfosuccinates, such as Anionyx 12s (Stepan); phosphate esters, such as Bio-SURF pbc-430 (Lonza); sulfated ethoxylates of fatty alcohols, such as Avirol SA-4110 (Henkel); and N-acyl-N-alkyl taurates, such as Igepon T (GAF).

Examples of useful cationic emulsifiers include quaternary ammonium salts, such as Algepon AK (Sandoz); and alkylated pyridinium salts, such as Damox 1010 (Ethyl).

Examples of useful nonionic emulsifiers include alkanolamides, such as Comperlan KD (Henkel); ethoxylated fatty alcohols, such as Brij (ICI); alkyl phenol polyethoxylates, such as Triton X-100 (Rohm and Haas); fatty acid esters; glycerol esters and glycol esters, such as Cutine GMS (Henkel); esters of propylene glycol, sorbitan and ethoxylated sorbitan, such as Tween 60 (ICI) and Span 20 (ICI).

Examples of useful amphoteric emulsifiers include betaines, such as Amphosol (Stepan); and alkyl amine oxides, such as Admox 1214 (Ethyl).

Other useful emulsifiers include polymeric surfactants, such as cellulose deriviatives; silicone surfactants (dimethylsiloxane polymers with hydrophile); and perfluorocartoxylic acid salts and fluorosurfactants.

Other useful emulsifiers are identified by Piirma, I., in *Polymeric Suffactants*, Marcel Dekker, New York (1992), and in U.S. Pat. Nos. 4,960,814, 4,911,736 and 4,846,986.

Cellulose derivatives have been found to be preferred emulusifiers, and methylcellulose is a more preferred emulsifier.

The emulsifier can be added to the mixture of the organic solution and the aqueous solution in any manner. For example, it can be added neat to either the aqueous solution or to the organic solution, or to a mixture of the two solutions. A preferred method of adding the emulsifier is to intermix the emulsifier with water to form an aqueous solution prior to mixing the aqueous solution with the organic solution. When methylcellulose is used as the emulsifier, it is preferred that it is intermixed into cold water in any manner that will result in the formation of an aqueous solution of the methylcellulose.

When the emulsifier is intermixed with the aqueous solution, it can be used in any amount that will result in the formation of a desired emulsion between the organic and aqueous solutions. It is preferred that the amount of the emulsifier in the aqueous solution be from about 0.1% to about 20% by weight, more preferred from about 0.2% to about 10% by weight, and even more preferred from about 0.5% to about 3% by weight of the aqueous solution.

The amount of emulsifier that is useful in the novel method can also be expressed on the basis of the amount of the lignin derivative. On this basis, any amount of the emulsifier can be used that will result in the formation of a desired emulsion between the organic and aqueous solutions. It is preferred that an amount of the emulsifier be used that provides a weight ratio between the emulsifier and the lignin derivative, on a dry basis, of from about 1:1 to about 1:100, more preferred is an emulsifier-to-lignin derivative weight ratio of from about 1:2 to about 1:50, even more preferred is a ratio of about 1:5 to about 1:20, and yet more preferred is a ratio of about 1:10 to about 1:15.

The organic solvent that is useful in the method of the present invention can be any solvent that has a normal boiling point that is lower than the normal boiling point of water and has a low solubility in water. It is preferred that the organic solvent is one that has a normal boiling point of from about 0° C. to about 100° C. and a solubility in water of less than about 20 g/100 ml at 20° C., more preferred that the organic solvent is one that has a normal boiling point of from about 20° C. to about 90° C. and a solubility in water of less than about 10 g/100 ml at 20° C., and even more preferred that the organic solvent is one that has a normal boiling point of from about 30° C. to about 80° C. and a solubility in water of less than about 5 g/100 ml at 20° C.

Organic solvents that are useful in the present method include methylene cholride, choroform, ethylacetate, cyclopentane, pentane, 2-methylbutane, methyl cyclopentane, hexane, cyclohexane, heptane, 2-methylpentane, 3-methylpentane, 2-methylhexane, 3-methylhexane, 2,3-dimethylbutane, methylcyclohexane, 2,3-dimethylpentane, 2,4-dimethylpentane, benzene, 1-pentene, 2-pentene, 1-hexene, 1-heptene, cyclohexene, 1-butanol, ethyl vinyl ether, propyl ether, isopropyl ether, butyl vinyl ether, butyl ethyl ether, 1,2-epoxybutane, furan, tetrahydropyran, 1-butanal, 2-methylpropanal, 2-pentanone, 3-pentanone, cyclohexanone, fluorobenzene, hexafluorobenzene, ethyl formate, propyl formate, isopropyl formate, vinyl acetate, isopropyl acetate, ethyl propionate, methyl acrylate, ethyl acrylate, methyl methacrylate, cloroethane, 1-chloropropane, 2-chloropropane, 1-chlorobutane, 2-chlorobutane, 1-chloro-2methylpropane, 2-chloro-2-methylpropane, 1-chloro-3-methylbutane, 3-chloropropene, tetrachloromethane, 1,1-dichloroethane, 1,2-dichloroethane, 1,2-dichloropropane, 1,1,1-trichloroethane, 1,1-dichloroethylene, 1,2-dichloroethylene, trichloroethylene, bromoethane, 1-bromopropane, 2-bromopropane, 1-bromobutane, 2-bromobutane, 2-bromo-2-methylpropane, bromoethylene, iodomethane, iodoethane, 2-iodopropane, trichlorofuoromethane, dichlorofuoromethane, dibromofluoromethane, bromochloromethane, bromochlorofluoromethane, 1,1,2-trichloro-1,2,2-trifluoroethane, 1,1,2,2-tetrachlorodifluoroethane, 1,2-dibromotetrafluoroethane, 1,2-dibromo, 1,1-difloroethane, 1,1-dichloro-2,2-difluoroethylene, propionitrile, acrylonitrile, methacrylonitrile, triethylamine, carbon disulfide, 1-butanethiol, methyl sulfide, ethyl sulfide, and tetramethylsilane. Any of these solvents can be used alone or in a mixture with any one or more of the other solvents.

Methylene chloride, chloroform and ethylacetate are preferred solvents, and methylene chloride has been found to be a more preferred solvent.

Lignin derivatives that are useful for forming a matrix for the matrix microparticles of the present invention include those that are soluble in the organic solvent in an amount of at least about 1% by weight at 20° C. When the terms "lignin derivative" are used herein, such terms are meant to include native lignins and any materials that are derived from native lignin, which meet the organic solubility criteria that is required for the material. It is preferred that the lignin derivative is one that is soluble in the organic solvent in an amount of at least about 10% by weight at 20° C. A preferred lignin derivative comprises lignin acetate.

The present matrix microparticles contain an agricultural active. When the terms "agricultural active" are used herein, they are meant to include any compound that directly or indirectly has a beneficial effect on a plant or its propagation material. For example, the terms agricultural active are meant to include herbicides, pesticides, fertilizers, growth factors, and the like.

The preferred agricultural active of the present invention is one that is soluble in water at 20° C. in an amount of less than about 2% by weight and is soluble in the organic solvent in an amount of at least about 1% by weight, and more preferred is an active that is soluble in water at 20° C. in an amount of less than about 2% by weight and is soluble in the organic solvent in an amount of at least about 5% by weight.

The preferred agricultural active is one that also is sufficiently compatible with the lignin derivative that no crystals of the active form during the production of the subject microparticles when the active is present in an amount of at least about 5% by weight of the lignin derivative. It is more preferred that the active is sufficiently compatible with the lignin derivative that no crystals of the active form during the production of the subject microparticles when the active is present in an amount of at least about 10% by weight, even more preferred is an active where no crystals form when the active is present in an amount of at least about 20% by weight of the lignin derivative.

Useful agricultural actives in the present invention include materials selected from the group consisting of pesticides, herbicides and growth regulators. Examples of useful actives include acylalanines, alkanamides, amidines, anilides, anilinopyrimidines, aromatic hydrocarbons, chlorophenyls, arylaminopropionic acids, aryloxyalkanoic acids, aryloxylkanoic acids, aryloxyphenoxypropionates, auxins, avermectins, benzamides, benzenecarboxilic acids, benzilates, benzimidazoles, benzofurans, benzoic acids, benzonitriles, benzothiadiazinones, benzothiazolones, benzotriazines, benzoylureas, bipyridyliums, biscarbamates, butyrolactones, carbamates, carbamoyltriazoles, chloroacetamides, chloronitriles, chloronicotinyls, cinnamic acids, coumarin anticoagulants, cyclodiene organochlorines, cyclohexanedione oximes, cytokinins, diacylhydrazines, dicarboximides, 2-dimethylaminopropane-1,3-dithiols, dimethyldithiocarbamates, dinitroanilines, dinitrophenols, diphenyl ethers, dithiocarbamates, DMI:imidazoles, DMI:pyridines, DMI:pyrimidines, DMI:triazoles, gibberellins, glycine derivatives, guanidines, halogenated alkanoic acids, hydroxyanilides, hydroxylbenzonitriles, imidazoles, imidazolinones, indandione anticoagulants, isoxazoles, isoxazolidinones, juvenile hormone mimics, MBI:dehydrases, morpholines, multisite:alkylenebis(dithiocarbamates), multisite: chloronitriles, multi-site: dimethyldithiocarbamates, multi-site: guanidines, multi-site: inorganics, multi-site: phenylphridinamines, multi-site: phosphonates, multi-site: phthalimides, multi-site: quinones, multi-site: sulphamides, natural pyrethrins, neonicotinoids, nitromethylene: neocorticoids, non-ester pyrethroids, N-phenyl carbamates, N-phenylphthalimides, organoarsenics, organochlorines, organophosphorous compounds, organotins, oxadiazines, oxadiazoles, oxathlins, oxozolidinediones, oxazolidinones, oxime carbamates, oxyacetamides, phanylamide: acylalanines, phenylamide: butyrolactones, phenylamide: oxazolidinones, phenylpyrazole herbicides, phenypyrazole insecticides, phenylpyridazines, phenylpyridinamines, phenylpyrroles, phenylureas, pheromones, phosphinic acids, phosphonates, phosphoroamidates, phosphorodithioates, phosphorothiolates, phthalamates, phthalimides, piperazines, polyoxins, pyrazoles, pyrazoliums, pyrethrins, pyrethroids, pyrethroid non-esters, pyridazinones, pyridazinones, pyridazinone analogues, pyridines, pyridinecarboxamides, pyridinecarboxylic acids, pyrimidindiones, pyrimidines, pyrimidinols, pyrimidinyl carbinols, pyrimidinyloxybenzoic compounds, pyrimidinyloxybenzoic analogues, quaternary ammonium compounds, quinolines, quinolinecarboxylic acids, quinones, semi-carbazones, strobilurin type compounds, sulfonylaminocarbonyltriazolinones, sufonylureas, sulfamides, synthetic auxins, tetrazines, tetrazolinones, thiadiazoles, thiocarbamates, 1,3,5-triazines, 1,2,4-triazinones, triazoles, triazolinones, triazolpyrimidines, triketones, uracils and ureas.

Examples of useful strobilurin type compounds include metominostrobin, picoxystrobin, famoxadone, azoxystrobin, kresoxim-methyl and trifloxystrobin.

Examples of useful neonicotinoids include acetamiprid, imidacloprid and thiamethoxam.

Examples of useful herbicides include phenoxy acetic acids, such as 2,4-D and MCPA; phenoxy propionic acids, such as dichlorprop (2,4-DP) and mecoprop (MCPP); phenoxy butyric acids, such as 2,4-DB and MCPB; benzoic acids, such as dicamba (Banvel, Clarity, Vanquish); picolinic acid and related compounds, such as picloram (Tordon), triclopyr (Garlon, Grandstand, Remedy, Turflon); clopyralid (Lontrel, Reclaim, Stinger, Transline), and quinclorac (Facet); naptalam (Alanap); semicarbones, such as diflufenzopyr-sodium (BAS 654, Distinct); chloro-s-triazines, such as atrazine (Aatrex, Atrazine), simazine (Princep), and cyanazine (Bladex); methoxy-s-triazines, such as prometon (Pramitol); methylthio-s-triazines, such as ametryn (Evik), and prometryn (Caparol, Cotton-Pro, Gesagard); other triazines, such as hexazinone (Velpar), and metribuzin (Sencor, Lexone); substituted ureas, such as diuron (Karmex), fluometuron (Cotoran), linuron (Lorox), and tebuthiuron (Spike); uracils, such as bromacil (Hyvar), and terbacil (Sinbar); benzothiadiazoles, such as bentazon (Basagran); benzonitriles, such as bromoxymil (Buctril); phenylcarbamates, such as desmedipham (Betanex), and phenmedipham (Spinaid); pyridazinones, such as pyrazon (Pyramin); phenypyriddazines, such as pyridate (Tough, Lentagran); propanil (Stam, Stampede); amitrole (Amitrol T); clomazone (Command); fluridone (Sonar); pyridazinones, such as norflurazon (Zorial, Evital, Solicam, Predict); isoxazoles, such as isoxaflutole (Balance); dinitroanilines, such as benefin (Balan), ethalfluralin (Sonalan, Curbit), oryzalin (Surflan), pendimethalin (Prowl, Pendulum, Pentagon), prodiamine (Barricade, Endurance, Factor), and trifluralin (Treflan Trifluralin); pyridines, such as dthiopyr (Dimension), and thiazopyr (Visor); amides, such as pronamide (Kerb); DCPA (Dacthal); carbamothioates (thiocarbamates), such as EPTC (Eptam, Eradicane, Eradicane Extra), cycloate (Ro-Neet), pebulate (Tillam), and triallate (Far-Go, Avandex BW), butylate (Sutan+), molinate (Ordram), thiobencarb (Bolero, Abolish), and vernolate (Vernam); seedling root inhibiting amides, such as napropamide (Devrinol); seedling root inhibiting phenylureas, such as siduron (Tupersan); bensulfide (Prefar, Betasan, Bensumec); chloroacetamides, such as acetochlor (Harness, Surpass, Topnotch); dimetenamid (Frontier), propachlor (Ramrod); alachlor (Lasso, Micro-Tech, Partner), and metolachlor (Dual, Pennant); glyphosate (Roundup, Rodeo); sulfosate (Touchdown); sulfonylureas, such as bensulfuron (Londax), chlorsulfuron (Glean, Telar), halosulfuron (Permit, Battalion, Manage), nicosulfuron (Accent), prosulfuron (Peak), rimsulfuron (Matrix, Elim, Titus, Prism), thifensulforon (Pinnacle), tribenuron (Express), chlorimuron (Classic), ethametsulfuron (Muster), metsulfuron (Ally, Escort), primisulfuron (Beacon), oxasulfuron (Expert), triasulfuron (Amber), and triflusulfuron (Upbeet); imidazolinones, such as imazamethabenz (Assert), imazamox (Raptor), imazapic (Cadre, Contend), imazapyr (Arsenal, Chopper, Stalker), imazaquin (Scepter, Image) and imazethapyr (Pursuit); aryoxyphenoxyproprionates, such as diclofop-methyl (Hoelon, Hoe-Grass, Illoxan), fenoxaprop-ethyl (Acclaim, Horizon, Excel), fenoxaprop-p-ethyl (Option II, Puma, Whip 360, Horizon), fluazifop-p-butyl (Flusilade 2000), haloxyfop (Verdict, Gallant), and quizalofop-p-ethyl (Assure II); cyclohexanediones, such as clethodim (Envoy, Prism, Select), sethoxydim (Poast, Poast Plus, Prestige, Torpedo, Ultims, Vantage), and tralkoxydim (Achieve); nitriles, such as dichlobenil (Casoron, Dyclomec); benzamides, such as isoxaben (Gallery); quinclorac (Facet); dilute sulfuric acid; monocarbamide dihydrogen sulfate (Enquick); herbicidal oils; bipyridyliums, such as diquat (Diquat, Reward), and paraquat (Gramoxanone Extra, Cyclone, Starfire); diphenylethers, such as aciflurofen (Blazer, Status), fomesafen (Flexstar, Reflex), lactofen (Cobra), and oxyfluorfen (Goal); oxidiazoles, such as fluthiacet (Action), and oxadiazon (Ronstar); n-phenylheterocycles, such as carfentrazone (Affinity, Aim), flumiclorac (Resource), and sulfentrazone (Authority, Cover, Spartan); glufosinate (Finale, Liberty, Rely); organic arsenicals, such as DSMA, and MSMA; asulam (Asulox); endothall (Accelerate, Aquathol, Des-I-Cate); ethofumesate (Nortron, Prograss); fosamine (Krenite); difenzoquat (Avenge); and TCA (Nata).

Examples of useful fungicides and fungicidal mixtures include fludioxonil, fluquinconazole, silthiopham, difenoconazole, a mixture of fludioxonil and fluquinconazole or 4,5-dimethyl-N-2-propenyl-2-(trimethylsilyl)-3-thiophencarboxamid; a mixture of difenoconazole and fluquinconazole or 4,5-dimethyl-N-2-propenyl-2-(trimethylsilyl)-3-thiophencarboxamid; and a mixture as taught in WO 00/27200 of a thienol[2,3-d]pyrimidin-4-one and an azole fungicide, an anilinopyrimidine fungicide, a morpholine fungicide, a strubilurin compound, a pyrrole compound, a phenylamide, or a dithiocarbamate fungicide.

Preferred agricultural actives include imidacloprid, acetamiprid, thiamethoxam, TI-435 (clothiamidin), simeconazole, fluquinconazole, tebuconazole, silthiopham, terbufos, chlorpyrifos, fipronil, chlorethoxyfos, tefluthrin, fipronil, carbofuran, tebupirimfos, methoprene, hydroprene, and mixtures thereof. Imidacloprid has been found to be particularly preferred as the agricultural active of the present invention.

When imidacloprid is an agricultural active in the subject matrix microcapsules, it has been found to be preferred that the organic solvent comprises methylene chloride and the lignin derivative comprises lignin acetate.

When the aqueous solution and the organic solution are intermixed, they can be mixed by any method that is known in the art to provide an emulsion. It is preferred that the step of forming an emulsion includes mixing the aqueous solution and the organic solution under conditions of high shear and thereby forming an oil-in-water emulsion wherein the organic solution forms the discontinuous phase and the aqueous solution forms the continuous phase.

During the time that high shear is being applied to the mixture, it is preferred that the temperature of the solutions be maintained sufficiently low that a significant amount of the organic solvent is not lost by evaporation. It is more preferred that the temperature of the aqueous solution and the organic solution is maintained at a level that is no higher than 20° C. below the normal boiling point of the organic solvent during the step comprising forming an emulsion, and yet more preferred that the temperature is maintained at a level that is no higher than 30° C. below the normal boiling point of the organic solvent.

When the organic solvent that is used includes methylene chloride, which has a normal boiling point of about 40.1° C., and the agricultural active includes imidacloprid, and lignin acetate is at least a major component of the lignin derivative, it is preferred that the temperature is maintained below about 10° C., and more preferred that the temperature be maintained at about 4° C. during formation of the emulsion.

When the emulsion is formed from the aqueous solution and the organic solution, the emulsion comprises discrete, substantially spherical droplets of a discontinuous phase dispersed within a continuous phase. As discussed above, it is preferred that the aqueous phase form the continuous phase and the organic phase—containing the lignin derivative and the agricultural active—form the droplets of the discontinuous phase. It is preferred that the organic solution in the discontinuous phase comprises droplets having an average diameter of no larger than about 100 microns. Smaller droplets are also preferred.

After the formation of the emulsion, the liquid droplets of the organic phase are transformed into solid spherical matrix microparticles by the removal of the organic solvent from the emulsion. Although the solvent can be removed from the emulsion by any means known in the art, evaporation is commonly used to remove the solvent.

When the solvent is removed by evaporation, it has been found to be preferred to carry out the evaporation at a rate that is sufficiently slow to permit the formation of matrix microparticles having a matrix of the lignin derivative throughout which is dispersed the agricultural active, the microparticles also having a majority of the active within the microparticles, rather than on the surface of the microparticles or as crystals in the aqueous solution. The presence of a significant portion of the active on the surface of the microparticles or as crystals in the aqueous solution results in the preparation having a high "REA" value. After formation of the emulsion, it is preferred to raise the temperature of the emulsion to increase the evaporation of the solvent, but to limit the temperature to below the normal boiling point of the solvent.

When the matrix microparticles are formed by the removal of the solvent, it is preferred that the microparticles are predominantly spherical and have an average diameter of less than about 100 microns, more preferred that they have an average diameter of less than about 25 microns, even more preferred that they have an average diameter of less than about 10 microns. The small spherical microparticles of the present invention do not have to be of the same size, but may be of different sizes within a size range. When it is said that the microparticles have an average diameter, it is a number average diameter that is referred to.

An advantage of microparticles of such small size is that they may be used in seed coating formulations that have a high degree of adhesion to the seed. It is known that larger particles, for example, larger than about 100 microns in average size, are more susceptible to abrasion and loss from the surface of the seed. Furthermore, smaller particles permit a more even distribution of the active over the surface of a seed or a plant, and also formulations that contain the microparticles are easier to process through application equipment such as seed coaters, sprayers, and the like.

The regular spherical shape of the microparticles of the present invention is also advantageous, because it insures that the release of the active from the particle occurs in a steadier and more predictable pace that if the particles were irregular in shape. When it is said that the active is distributed throughout the lignin-based matrix, it should be understood that the distribution does not have to be of any particular pattern (i.e., not necessarily homogeneous or evenly distributed) and can be more at the center, or nearer the surface, and the active distribution in the matrix can be a molecular mix or can be particles of the active distributed within the solid lignin derivative matrix.

Unlike many of the lignin-based particles of the prior art, the present method of producing the novel matrix microparticles is free of grinding or milling. The present matrix microparticles are generally spherical in shape, and it is preferred that a preparation of the microparticles has a level of readily extractable active (REA) that is lower than about 20%.

An advantageous feature of the present microparticles is the surprising combination of their small size and their ability to continue to release active over an unexpectedly long period of time. Small lignin-based microparticles of the prior art are reported to release most active material within a few days, whereas the present microparticles are found to be capable of releasing the agricultural active into an infinite sink of water at room temperature for at least 1000 hours.

The present matrix microparticles can be used in the same manner as any other conventional microparticle or microcapsule that is designed for the controlled release of an agricultural active. The subject microparticles can be used to treat a plant or its propagation material by contacting the plant or its propagation material with a formulation that contains the microparticles. By the terms "plant or its propagation material", it is meant to include any and all parts of a plant in any stage of growth, as well as any root, shoot, seed, flower, inflorescence, tuber, rhizome, and any other material from which the plant can be started or regenerated. When it is said that the microparticles are "contacted" with the plant or its propagation material, it is meant to include all direct and indirect contact, such as, for example, application to the plant, seed, or to the soil in which the seed or plant has been or is to be planted.

The microparticles can be applied in a dry formulation, or can be applied as a slurry or emulsion. They can be used neat or can be mixed with any other materials that can be useful components of seed or plant treatment formulations. Such materials can include stickers, safeners, herbicides, pesticides, growth regulators, colorants, dyes, stabilizers, surfactants, antioxidants, and the like.

A particularly useful application of the present microparticles is for the treatment of plant seed. It is preferred that the microparticles are applied to the seed after the seed have been harvested from the parent plant and before they are themselves planted.

As mentioned above, other conventional inactive or inert ingredients can be incorporated into the formulation. Such inert ingredients include but are not limited to: conventional sticking agents, dispersing agents such as methylcellulose (Methocel A15LV or Methocel A15C, for example, serve as combined dispersant/sticking agents for use in seed treatments), polyvinyl alcohol (e.g., Elvanol 51-05), lecithin (e.g., Yelkinol P), polymeric dispersants (e.g., polyvinylpyrrolidone/vinyl acetate PVP/VA S-630), thickeners (e.g., clay thickeners such as Van Gel B to improve viscosity and reduce settling of particle suspensions), emulsion stabilizers, surfactants, antifreeze compounds (e.g., urea), dyes, colorants, and the like. Further inert ingredients useful in the present invention can be found in McCutcheon's, vol. 1, "*Emulsifiers and Detergents*," MC Publishing Company, Glen Rock, N.J., U.S.A., 1996. Additional inert ingredients useful in the present invention can be found in McCutcheon's, vol. 2, "*Functional Materials*," MC Publishing Company, Glen Rock, N.J., U.S.A., 1996.

The microparticle formulations of the present invention can be applied to seeds by any standard seed treatment methodology, including but not limited to mixing in a container (e.g., a bottle or bag), mechanical application, tumbling, spraying, and immersion. Any conventional active or inert material can be used for contacting seeds with microparticles according to the present invention, such as conventional film-coating materials including but not limited to water-based film coating materials such as Sepiret (Seppic, Inc., Fairfield, N.J.) and Opacoat (Berwind Pharm. Services, Westpoint, Pa.).

The subject microparticles can be applied to a seed as a component of a seed coating. Seed coating methods and compositions that are known in the art are useful when they are modified by the addition of the microparticles of the present invention. Such coating methods and apparatus for their application are disclosed in, for example, U.S. Pat. Nos. 5,918,413, 5,891,246, 5,554,445, 5,389,399, 5,107,787, 5,080,925, 4,759,945 and 4,465,017. Seed coating compositions are disclosed, for example, in U.S. Pat. Nos. 5,939,356, 5,882,713, 5,876,739, 5,849,320, 5,834,447, 5,791,084, 5,661,103, 5,622,003, 5,580,544, 5,328,942, 5,300,127, 4,735,015, 4,634,587, 4,383,391, 4,372,080, 4,339,456, 4,272,417 and 4,245,432, among others.

Useful seed coatings contain one or more binders in addition to the subject microparticles.

Binders that are useful in the present invention preferably comprise an adhesive polymer that may be natural or synthetic and is without phytotoxic effect on the seed to be coated. The binder may be selected from polyvinyl acetates; polyvinyl acetate copolymers; ethylene vinyl acetate (EVA) copolymers; polyvinyl alcohols; polyvinyl alcohol copolymers; celluloses, including ethylcelluloses, methylcelluloses, hydroxymethylcelluloses, hydroxypropylcelluloses and carboxymethylcellulose; polyvinylpyrolidones; polysaccharides, including starch, modified starch, dextrins, maltodextrins, alginate and chitosans; fats; oils; proteins, including gelatin and zeins; gum arabics; shellacs; vinylidene chloride and vinylidene chloride copolymers; calcium lignosulfonates; acrylic copolymers; polyvinylacrylates; polyethylene oxide; acrylamide polymers and copolymers; polyhydroxyethyl acrylate, methylacrylamide monomers; and polychloroprene.

The amount of binder in the coating can vary, but will be in the range of about 0.01 to about 25% of the weight of the seed, more preferably from about 0.05 to about 15%, and even more preferably from about 0.1% to about 10%.

The agricultural actives that are useful in the subject microparticles are those that are described above. The amount of active, and, therefore, the amount of microparticles, that is used for the treatment of a seed will vary depending upon the type of seed and the type of active ingredients, but the treatment will comprise contacting the seeds with an amount of the microparticles that is pesticidally, or otherwise, effective. When insects are the target pest, that amount will be an amount of an insecticidal active that is insecticidally effective. As used herein, an insecticidally effective amount means that amount of insecticide that will kill insect pests in the larvae or pupal state of growth, or will consistently reduce or retard the amount of damage produced by insect pests.

In general, the amount of agricultural active that is applied to the seed in the treatment will range from about 1 gm to about 2000 gm of the active ingredient of the pesticide per 100 kg of the weight of the seed. Preferably, the amount of pesticide will be within the range of about 10 gm to about 1000 gm active per 100 kg of seed, more preferably within the range of about 50 gm to about 800 gm active per 100 kg of seed, yet more preferably within the range of about 100 gm to about 550 gm active per 100 kg seed, and even more preferably within the range of about 200 gm to about 500 gm of active per 100 kg of seed weight. Alternatively, it has been found to be preferred that the amount of the pesticide be over about 60 gm of the active ingredient of the pesticide per 100 kg of the seed, and more preferably over about 80 gm per 100 kg of seed.

The microparticles of the subject invention can be applied to the seed in the form of a coating. The use of a coating is particularly effective in accommodating high pesticidal loads, as can be required to treat typically refractory pests, such as corn rootworm, while at the same time preventing unacceptable phytotoxicity due to the increased pesticidal load.

Optionally, a plasticizer can be used in the coating formulation. Plasticizers are typically used to make the film that is formed by the coating layer more flexible, to improve adhesion and spreadability, and to improve the speed of processing. Improved film flexibility is important to minimize chipping, breakage or flaking during storage, handling or sowing processes. Many plasticizers may be used, however, useful plasticizers include polyethylene glycol, glycerol, butylbenzylphthalate, glycol benzoates and related compounds. The range of plasticizer in the coating layer will be in the range of from bout 0.1 to about 20% by weight.

In addition to the coating layer, the seed may be treated with one or more of the following ingredients: other pesticides including fungicides and herbicides; herbicidal safeners; fertilizers and/or biocontrol agents. These ingredients may be added as a separate layer or alternatively may be added in the pesticidal coating layer.

The microparticle formulation may be applied to the seeds using conventional coating techniques and machines, such as fluidized bed techniques, the roller mill method, rotostatic seed treaters, and drum coaters. Other methods, such as spouted beds may also be useful. The seeds may be presized before coating. After coating, the seeds are typically dried and then transferred to a sizing machine for sizing. Such procedures are known in the art.

The microparticle-treated seeds may also be enveloped with a film overcoating to protect the coating. Such overcoatings are known in the art and may be applied using conventional fluidized bed and drum film coating techniques.

In yet another embodiment, a powdered form of the dry microparticles can be mixed directly with seed. Optionally, a sticking agent can be used to adhere the powder to the seed surface. For example, a quantity of seed can be mixed with a sticking agent and optionally agitated to encourage uniform coating of the seed with the sticking agent. The seed coated with the sticking agent can then be mixed with the dry microparticles. The mixture can be agitated, for example by tumbling, to encourage contact of the sticking agent with the dry microparticles, thereby causing the microparticles to stick to the seed.

The treated seeds of the present invention can be used for the propagation of plants in the same manner as conventional treated seed. The treated seeds can be stored, handled, sowed and tilled in the same manner as any other pesticide treated seed. Appropriate safety measures should be taken to limit contact of the treated seed with humans, food or feed materials, water and birds and wild or domestic animals.

Also included within the scope of this invention is a treated plant or its propagation material that includes a plant or its propagation material that has been contacted with the formulation containing the present lignin-based matrix microparticles.

The following examples describe preferred embodiments of the invention. Other embodiments within the scope of the claims herein will be apparent to one skilled in the art from consideration of the specification or practice of the invention as disclosed herein. It is intended that the specification, together with the examples, be considered to be exemplary only, with the scope and spirit of the invention being indicated by the claims which follow the examples. In the examples all percentages are given on a weight basis unless otherwise indicated.

Example 1

This example shows the production of lignin-based matrix microparticles for the controlled release of imidacloprid.

An aqueous solution of methyl cellulose (1.09 g; Methocel A15LV, available from Dow Chemical Co.) was prepared in a 400 ml beaker by mixing with 89.71 g of water, and the solution was cooled to 4° C. in an ice bath. An organic solution containing imidacloprid (1.7 g; available commercially in formulations under the trade names Admire®, Gaucho®, Confidor® and Winner®, all from Bayer AG), and lignin acetate (14.8 g; available from Aldrich) was prepared by mixing with methylenechloride (93.5 g, available from Aldrich) until all solids had gone into solution. The organic solution was then added to the aqueous solution in the beaker over a period of about 30 seconds, during which time the mixture in the beaker was agitated with a high shear mixer (Silverson, Model L4R) equipped with a 6-hole screen. The mixture was agitated with the high shear mixer for a total of 3 minutes at a setting of 3, during which time a milky white emulsion was formed. The emulsion was then removed from the ice bath and stirred for 20 hours with a mechanical stirrer while it was allowed to come to room temperature. During the 20 hours, the methylenechloride evaporated from the mixture, leaving 94.33 g of a white slurry of matrix microparticles. The microparticles had an average particle size of 7.3 microns as measured by a Coulter Counter.

Figure 1B:
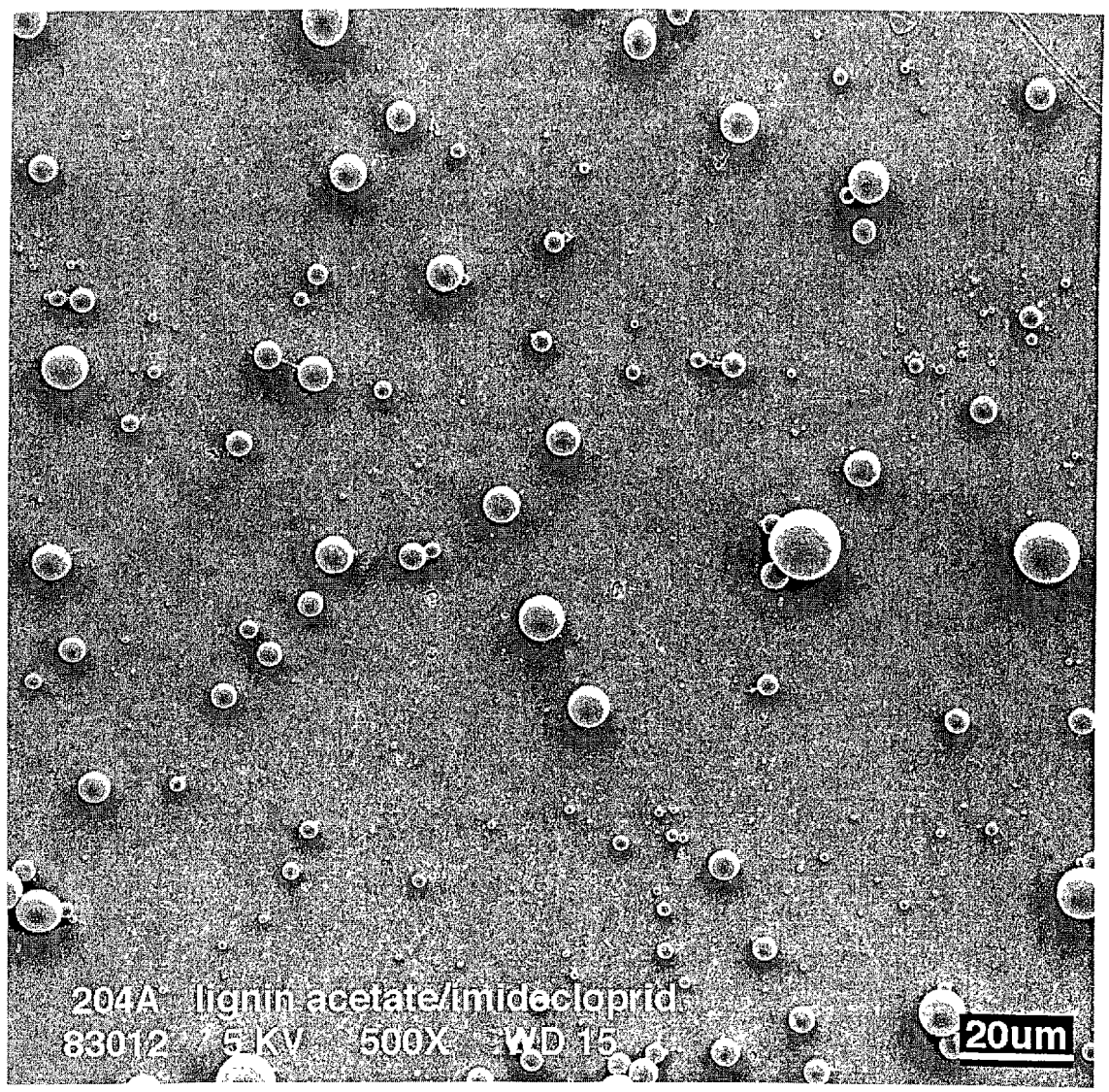
Figure 1C:
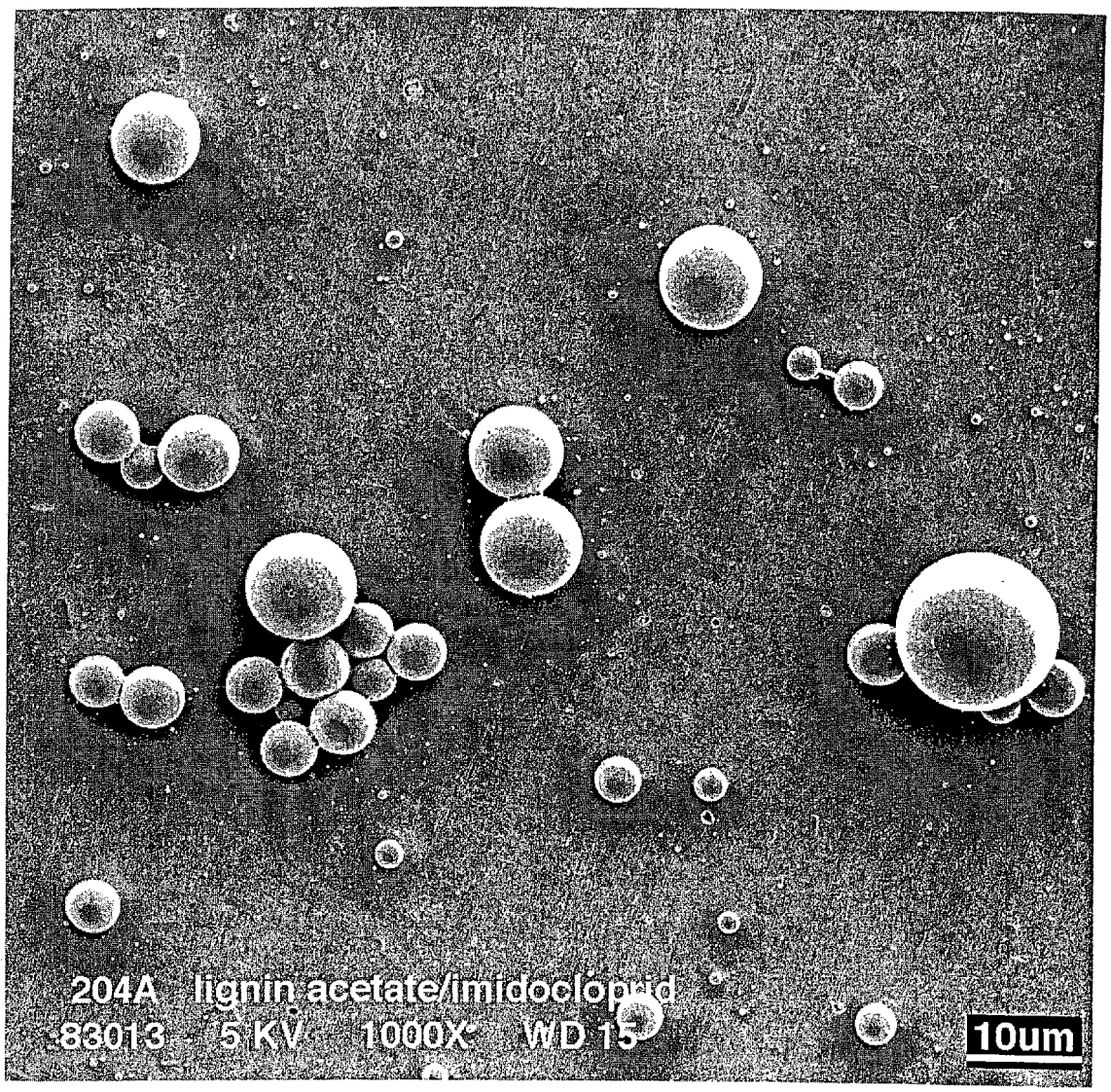
Figure 1D:
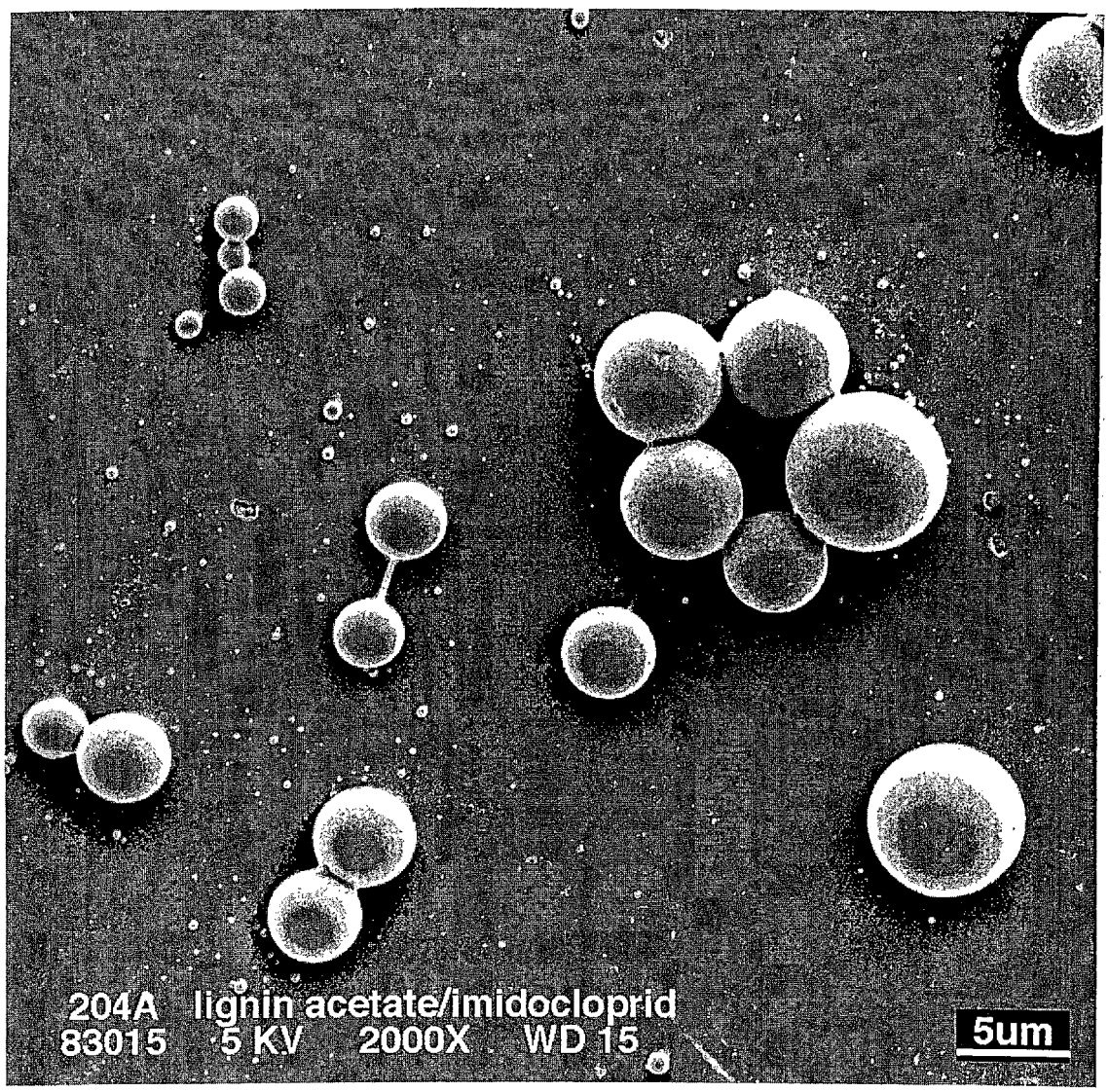
Figure 2:
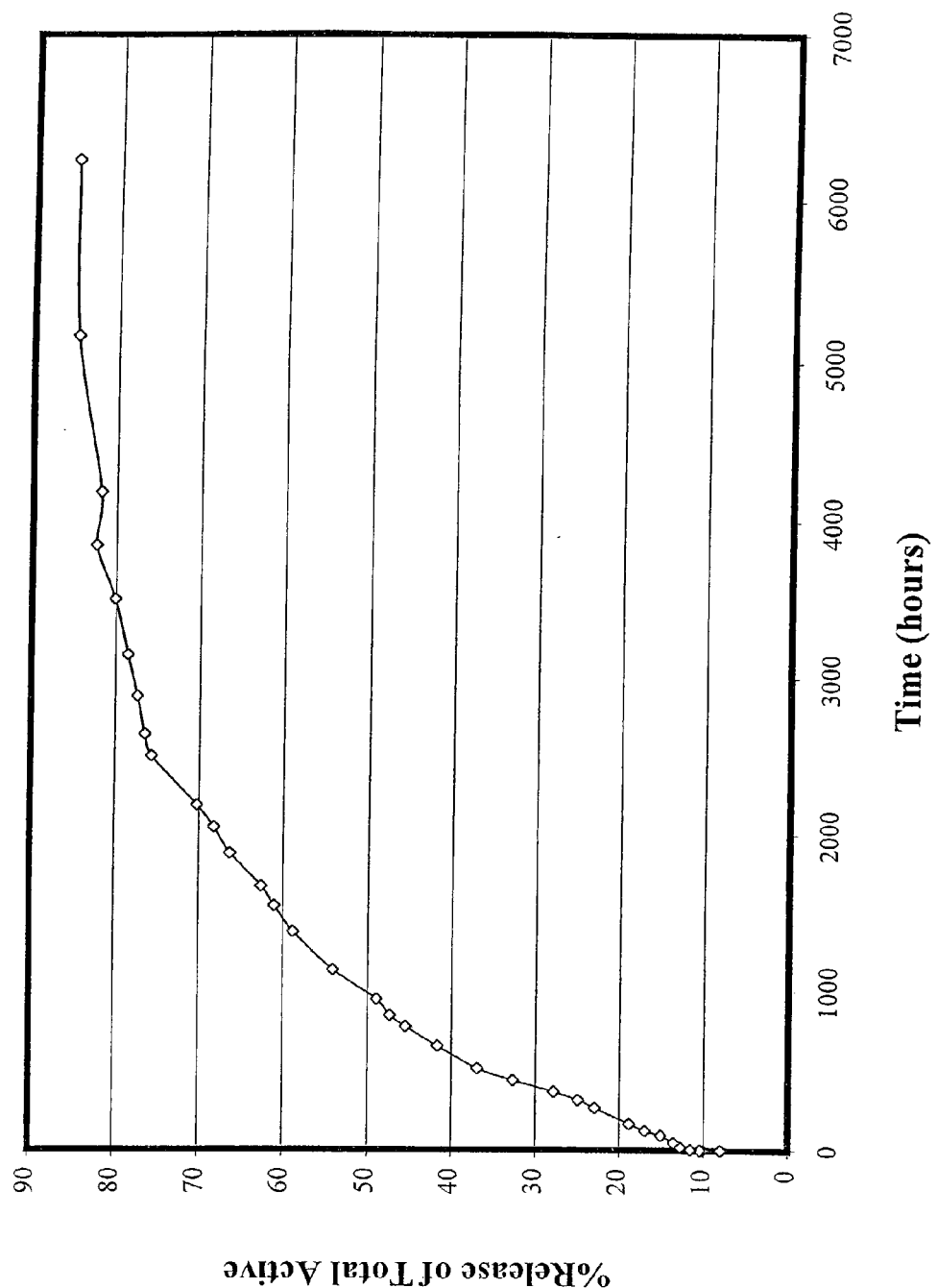
FIG. 2 shows a release rate curve for the release of imidacloprid from lignin-based matrix microparticles of the present invention into an excess of water at room temperature, and indicates a half-life of approximately 1000 hours.
Figure 3A:
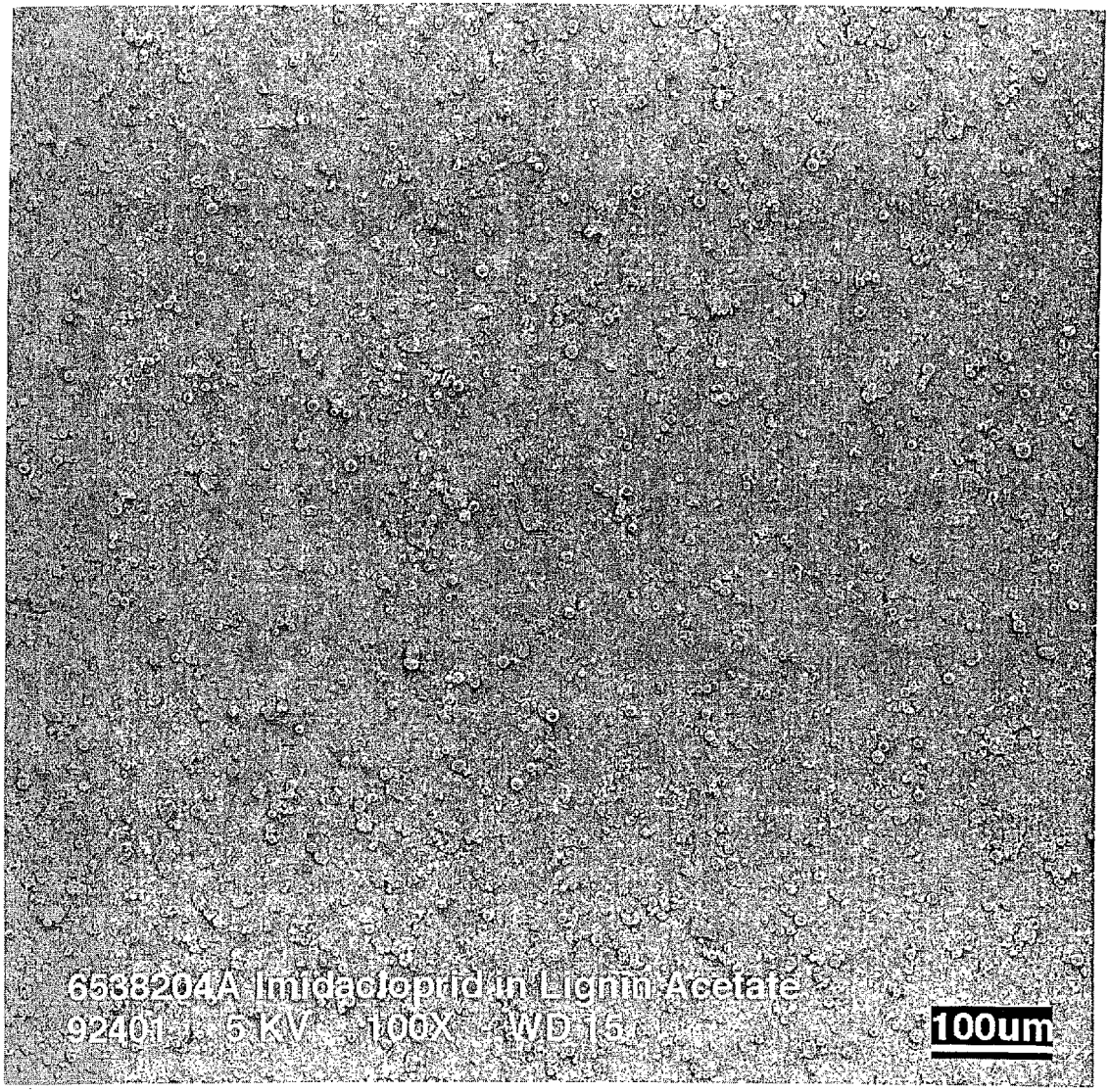
FIG. 3 shows electron micrographs of the microparticles shown in FIG. 1 after submersion in water for 42 days (about 1,000 hours) taken at magnifications of (a) 100×, (b) 500×, (c) 1000×, and (d) 2000×, wherein it is apparent that the microparticles were physically breaking down into cracked spheres or smaller fragments.
Figure 3B:
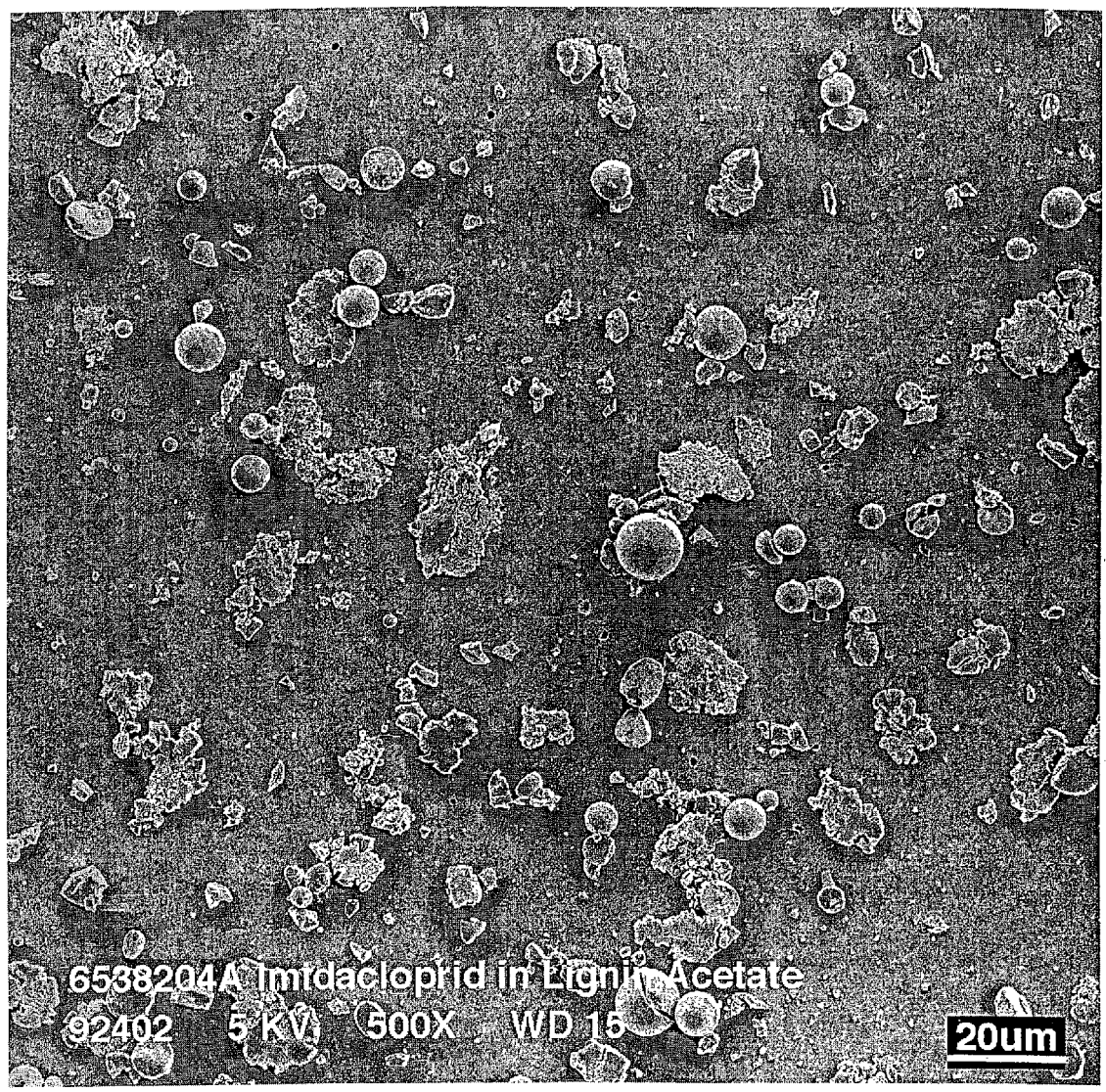
Figure 3C:
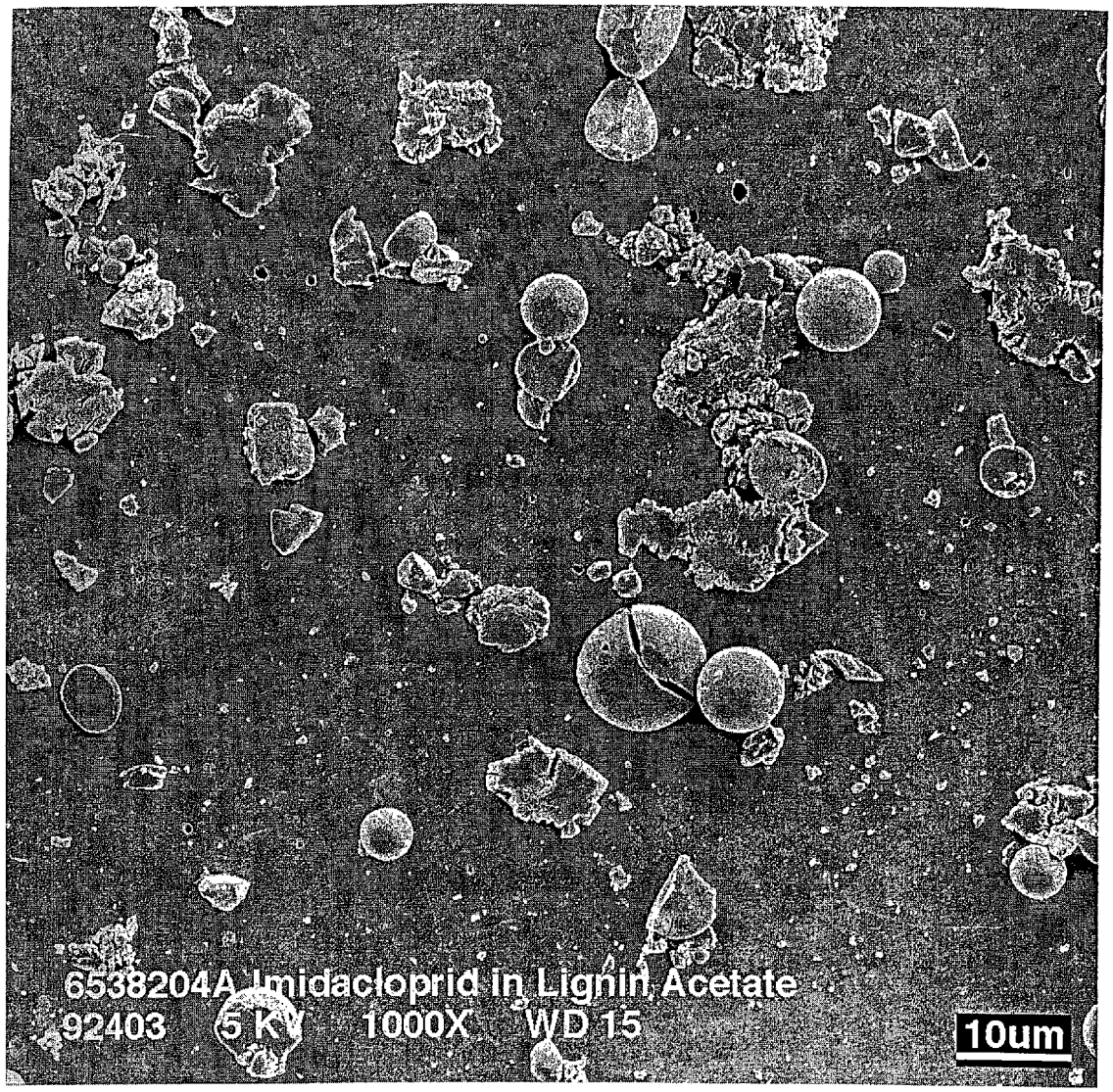
Figure 3D:
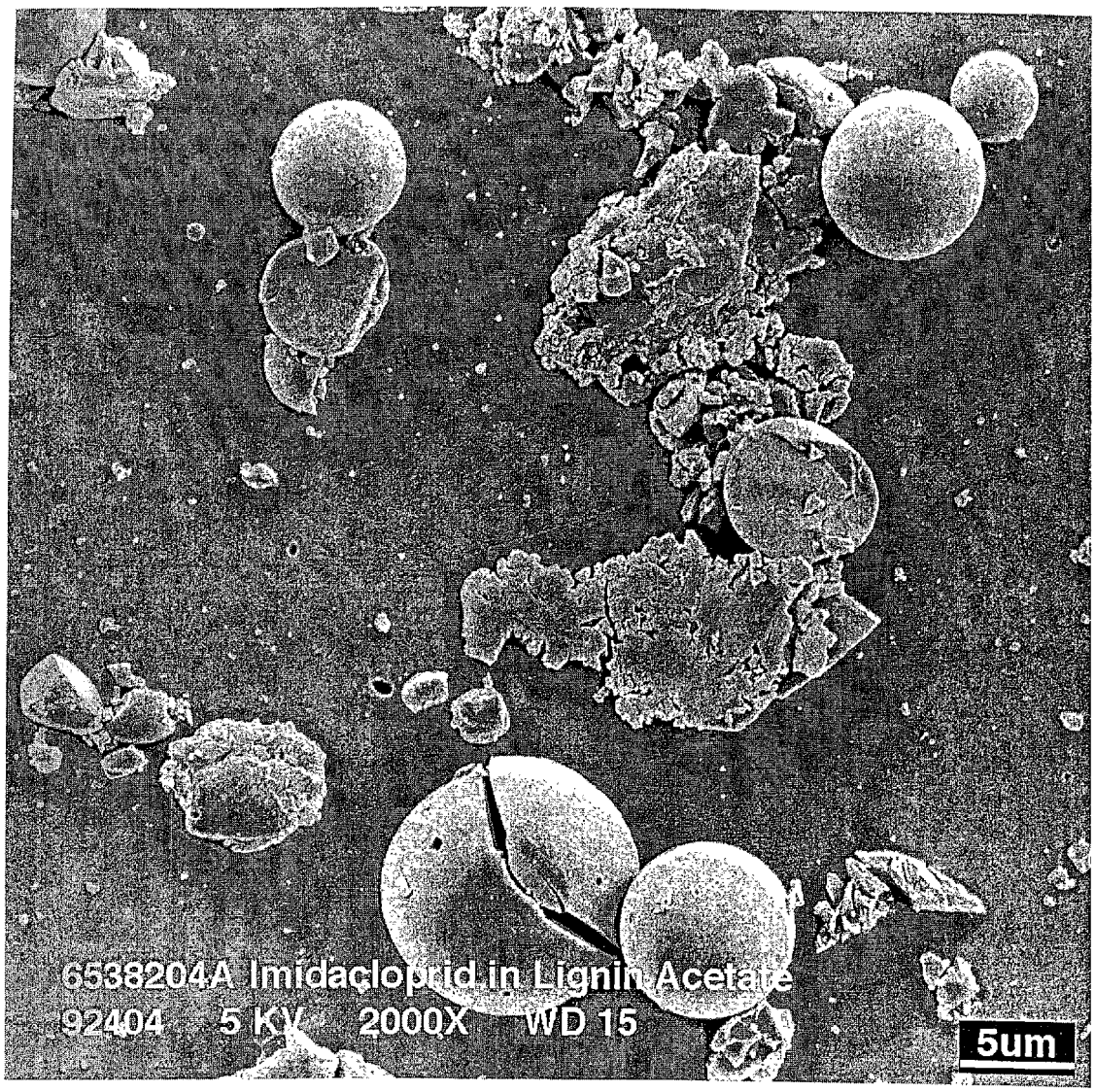
Figure 4:
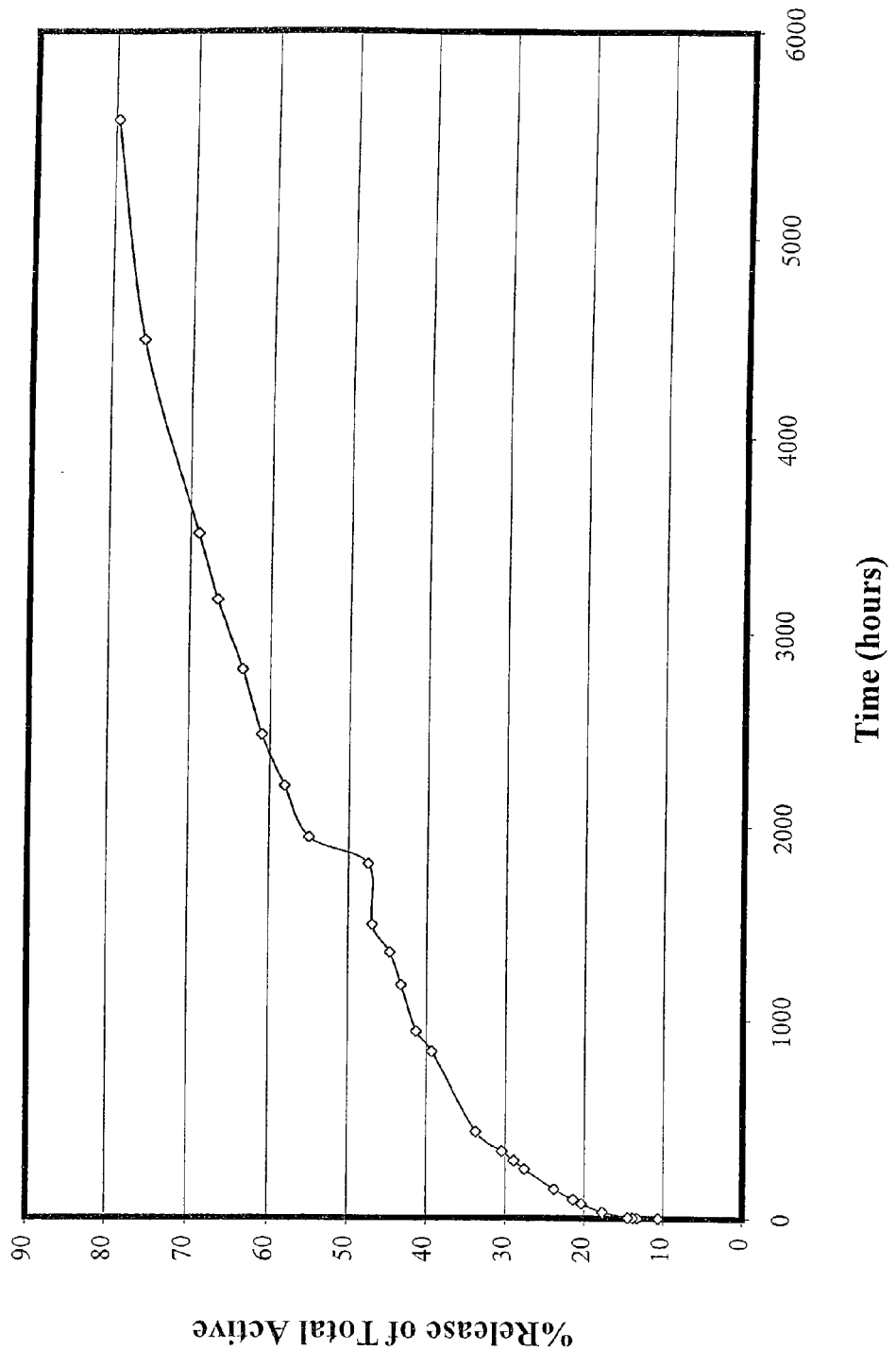
FIG. 4 shows a release rate curve for the release of imidacloprid from lignin-based matrix microparticles having a higher loading of imidacloprid than the microparticles of FIG. 2, where the release was measured into an excess of water at room temperature, and indicates a half-life of approximately 2000 hours.
Figure 5:
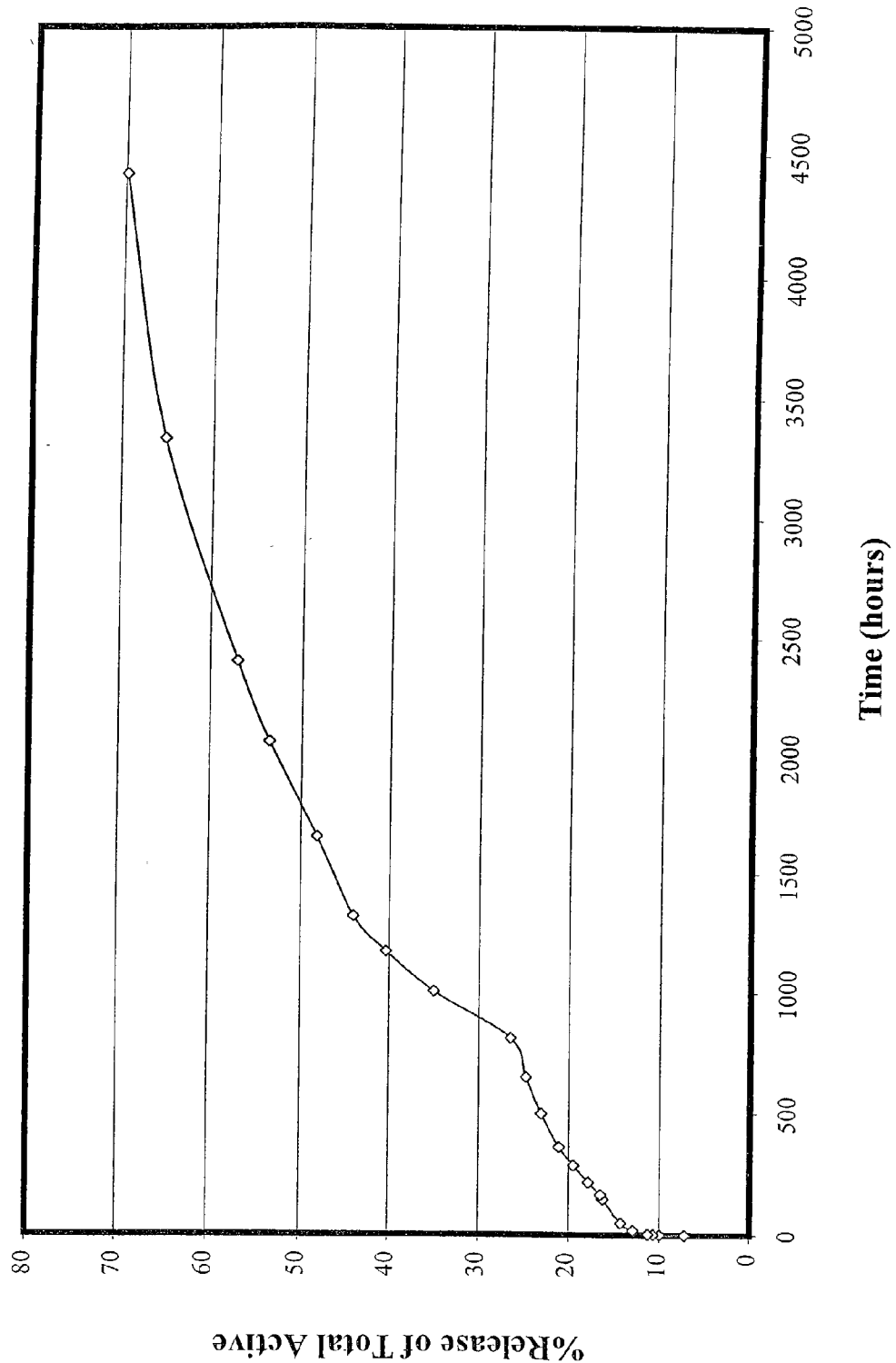
FIG. 5 shows a release rate curve for the release of imidacloprid from lignin-based matrix microparticles having a smaller size than the microparticles of FIG. 2, where the release was measured into an excess of water at room temperature, and indicates a half-life of approximately 2000 hours.
Figure 6:
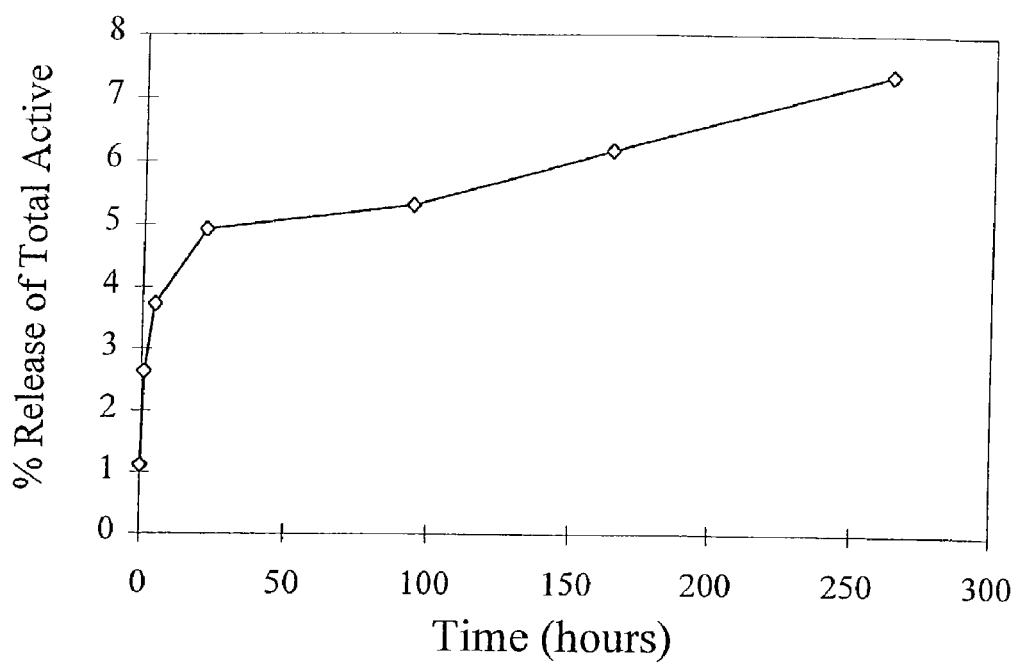
FIG. 6 shows a release rate curve for the release of silthiopham from lignin-based matrix microparticles of the present invention into an excess of water at room temperature.

Electron micrographs of the matrix microparticles were taken at increasingly higher magnification and showed that the microparticles were spherical particles having a distribution of sizes, but with few, or no, particles over about 20 microns in diameter. These microparticles are shown in FIG. 1 at magnifications of 100×(FIG. 1(a)), 500×(FIG. 1(b)), 1000×(FIG. 1(c)), and 2000×(FIG. 1(d)). Also noted in the micrographs was the almost total lack of free imidacloprid crystals in the slurry. This was interpreted to mean that the majority of the imidacloprid was retained within the microparticles and not free in solution.

The relative amount of the active that is released into the environment without control is termed the "readily extractable active" (REA). As used herein, REA means the percent by weight of the total active ingredient that was added to the formulation that dissolved in water in the following test:

REA was measured by adding the formulation to be tested to water in each of two test tubes at room temperature, about 25° C. The total amount of the formulation added to one test tube was sufficient to provide an amount of the active ingredient that was about 80% of its solubility limit in water at that temperature. The total amount of the formulation added to the other test tube was sufficient to provide an amount of the active that was about 120% of the solubility limit. Both tubes were then shaken vigorously for about 200 shakes. A sample of the mixture was removed from each tube and filtered through a 0.45 micron PTFE filter. The concentration of the active in the filtered liquid was measured in each of the two test tubes and the percentage of the total amount of active that had been released into the water was calculated. The value of the total amount of active that was released into the water was divided by the total amount of active that was initially added to the tube and the average of those values was multiplied by 100 and reported as percent REA for the formulation. In the present formulation, the active was imidacloprid, and the REA for the present microparticulate slurry was 8.3%. This reinforces the micrographs in indicating that most of the imidacloprid in the formulation was initially present within the microparticles and not free in the aqueous solution.

The rate of release of the imidacloprid was measured as a function of time by the following method. A measured amount of a controlled release formulation was mixed with an amount of water at room temperature so that the total concentration of active ingredient present in the aqueous mixture is no more than about ⅓ of the solubility limit of the active in water at room temperature—about 25° C. The mixture was then mixed in a beaker with a magnetic stirrer. At intervals, aliquots of the mixture were removed and filtered through a 0.45 micron PTFE filter. The amount of the active ingredient in the filtered solution was then measured. For example, when the active ingredient was imidacloprid, about 0.2 g/l total concentration of imidacloprid was added to the aqueous mixture and the concentration of imidacloprid was measured by reverse phase HPLC with UV detection.

The release rate of imidacloprid into an excess of water from the microparticles described above was measured for over 6000 hours, and the release rate is shown in FIG. 2. From the data, it appeared that the time required for the exhaustion of one-half of the imidacloprid from the microparticles (the half-life, or $t_{1/2}$) was about 1000 hours, which was considered to be a release period of long duration for such small particles.

After the slurry had been subjected to the release test for 42 days (about 1000 hours) a sample was taken and electron micrographs were again taken of the particles. As shown in FIG. 3, at successively higher magnifications of (a) 100×, (b) 500×, (c) 1000×, and (d) 2000×, it was apparent that the microparticles were physically breaking down into cracked spheres or smaller fragments. It is not known whether release of the imidacloprid resulted in weakening the microparticles, or whether water-induced breakdown of the microparticles resulted in release of the imidacloprid. However, the phenomena appeared to occur concurrently.

Example 2

This illustrates the formation of lignin-based matrix microparticles having a higher imidacloprid loading than in Example 1.

Lignin-based matrix microparticles for the controlled release of imidacloprid were produced as described in Example 1, except that 10.9 g of lignin acetate was used, instead of 14.8 g, and 97.4 g of methylenechloride was used, rather than 93.5 g. After the removal of methylenechloride, 64.25 g of a white slurry of microparticles was collected. The average particle size was 6.5 microns, and the REA was 11.4%. No crystals of imidacloprid were apparent in an electron micrograph of the slurry. The slurry was tested for release rate as described in Example 1, and the release rate curve shown in FIG. 4 indicated a $t_{1/2}$ of about 2000 hours.

Example 3

This illustrates the formation of lignin-based matrix microparticles having smaller size.

Lignin-based matrix microparticles for the controlled release of imidacloprid were produced as described in Example 1, except that the setting of the Silverson high shear device was operated at a setting of 5.5, rather than 3. The average particle size was reduced to 5.6 microns, and the REA was 7.2%. No crystals of imidacloprid were apparent in an electron micrograph of the slurry. The slurry was tested for release rate as described in Example 1, and the release rate curve shown in FIG. 5 indicated a $t_{1/2}$ of about 2000 hours.

Example 4

This illustrates the formation of lignin-based microparticles that contain silthiopham as the agricultural active.

Lignin-based matrix microparticles for the controlled release of silthiopham were produced as described in Example 1, except that the setting of the Silverson high shear device was operated at a setting of 5.5, rather than 3. The average particle size was 6.2 microns, and the REA was 1.1%. No crystals of silthiopham were apparent in an optical micrograph of the slurry.

The slurry was tested for release rate as described in Example 1 except that the active is silthiopham instead of imidacloprid, and the release rate curve is shown in FIG. 6.

Comparative Example 1

This illustrates the formation of microparticles for the controlled release of imidacloprid from a poly(methyl methacrylate) matrix.

An aqueous solution of methyl cellulose (1.09 g; Methocel A15LV, available from Dow Chemical Co.) was prepared in a 400 ml beaker by mixing with 89.71 g of water, and the solution was cooled to 4° C. in an ice bath. An organic solution containing imidacloprid (1.7 g; available commercially under the trade names Admire®, Gaucho®, Confidor® and Winner®, all from Bayer AG), and poly(methyl methacrylate), (PMMA), (14.80 g, having an average molecular weight of 120,000, and available from Aldrich), was prepared by mixing with methylenechloride (93.5 g, available from Aldrich) until all solids had gone into solution. The organic solution was then added to the aqueous solution in the beaker over a period of about 30 seconds, during which time the mixture in the beaker was agitated with a high shear mixer (Silverson, Model L4R) equipped with a 6-hole screen. The mixture was agitated with the high shear mixer for a total of 3 minutes at a setting of 3, during which time a milky white emulsion was formed. The emulsion was then removed from the ice bath and stirred for 20 hours with a mechanical stirrer while it was allowed to come to room temperature. During the 20 hours, the methylenechloride evaporated from the mixture, leaving 93.8 g of a white slurry of matrix microparticles. Microscopic examination of the slurry showed that microspheres had been formed, but also showed the presence of many crystals that were presumably free imidacloprid that had not been incorporated into the microparticles.

It was concluded, therefore, that insufficient compatibility existed between the PMMA and imidacloprid to permit the successful formation of matrix microparticles for controlled release of imidacloprid.

All references cited in this specification, including without limitation all papers, publications, patents, patent applications, presentations, texts, reports, manuscripts, brochures, books, internet postings, journal articles, periodicals, and the like, are hereby incorporated by reference into this specification in their entireties. The discussion of the references herein is intended merely to summarize the assertions made by their authors and no admission is made that any reference constitutes prior art. Applicants reserve the right to challenge the accuracy and pertinency of the cited references.

In view of the above, it will be seen that the several advantages of the invention are achieved and other advantageous results obtained.

As various changes could be made in the above methods and compositions without departing from the scope of the invention, it is intended that all matter contained in the above description and shown in the accompanying drawings shall be interpreted as illustrative and not in a limiting sense.

What is claimed is:

1. A method of producing lignin-based matrix microparticles for the controlled release of an agricultural active, the method comprising the steps of:

forming an emulsion of an organic solution in an aqueous solution, wherein the organic solution contains a lignin derivative which is soluble in methylene chloride in an amount of at least 1% by weight at 20° C. and an agricultural active in a volatile organic solvent and the aqueous solution contains an emulsifier which is selected from the group consisting of nonionic and amphoteric emulsifiers; and removing the organic solvent, thereby producing microparticles having a matrix comprising the lignin derivative within which the agricultural active is distributed.

2. The method according to claim 1, wherein the emulsifier is one that is compatible with the agricultural active and one in whose presence an oil-in-water emulsion is more stable than an emulsion in which the emulsifier is absent.

3. The method according to claim 2, wherein the emulsifier is selected from the group consisting of ethoxylated fatty alcohols, alkyl phenol polyethoxylates, fatty acid esters, glycerol esters, glycol esters, esters of propylene glycol, sorbitan and ethoxylated sorbitan, betaines, alkyl amine oxides, polymeric surfactants, silicone surfactants (dimethylsiloxane polymers with hydrophile), fluorosurfactants, and mixtures thereof.

4. The method according to claim 1, wherein the emulsifier is methylcellulose.

5. The method according to claim 1, wherein the organic solvent is one that has a normal boiling point of from about 0° C. to about 100° C. and a solubility in water of less than about 20 g/100 ml at 20° C.

6. The method according to claim 5, wherein the organic solvent is one that has a normal boiling point of from about 20° C. to about 90° C. and a solubility in water of less than about 10 g/100 ml at 20° C.

7. The method according to claim 6, wherein the organic solvent is one that has a normal boiling point of from about 30° C. to about 80° C. and a solubility in water of less than about 5 g/100 ml at 20° C.

8. The method according to claim 5, wherein the organic solvent is selected from the group consisting of methylene chloride, chloroform, ethylacetate, cyclopentane, pentane, 2-methylbutane, methyl cyclopentane, hexane, cyclohexane, heptane, 2-methylpentane, 3-methylpentane, 2-methylhexane, 3-methylhexane, 2,3-dimethylbutane, methylcyclohexane, 2,3-dimethylpentane, 2,4-dimethylpentane, benzene, 1-pentene, 2-pentene, 1-hexene, 1-heptene, cyclohexene, 1-butanol, ethyl vinyl ether, propyl ether, isopropyl ether, butyl vinyl ether, butyl ethyl ether, 1,2-epoxybutane, furan, tetrahydropyran, 1-butanal, 2-methylpropanal, 2-pentanone, 3-pentanone, cyclohexanone, fluorobenzene, hexafluorobenzene, ethyl formate, propyl formate, isopropyl formate, vinyl acetate, isopropyl acetate, ethyl propionate, methyl acrylate, ethyl acrylate, methyl methacrylate, cloroethane, 1-chloropropane, 2-chloropropane, 1-chlorobutane, 2-chlorobutane, 1-chloro-2methylpropane, 2-chloro-2-methylpropane, 1-chloro-3-methylbutane, 3-chloropropene, tetrachloromethane, 1,1-dichloroethane, 1,2-dichloroethane, 1,2-dichloropropane, 1,1,1-trichloroethane, 1,1-dichloroethylene, 1,2-dichloroethylene, trichloroethylene, bromoethane, 1-bromopropane, 2-bromopropane, 1-bromobutane, 2-bromobutane, 2-bromo-2-methylpropane, bromoethylene, iodomethane, iodoethane, 2-iodopropane, trichlorofluoromethane, dichlorofluoromethane, dibromofluoromethane, bromochloromethane, bromochlorofluoromethane, 1,1,2-trichloro-1,2,2-trifluoroethane, 1,1,2,2-tetrachlorodifluoroethane, 1,2-dibromotetrafluoroethane, 1,2-dibromo, 1,1-difloroethane, 1,1-dichloro-2,2-difluoroethylene, propionitrile, acrylonitrile, methacrylonitrile, triethylamine, carbon disulfide, 1-butanethiol, methyl sulfide, ethyl sulfide, tetramethylsilane, and mixtures thereof.

9. The method according to claim 5, wherein the organic solvent comprises methylene chloride.

10. The method according to claim 1, wherein the lignin derivative is one that is soluble in the organic solvent in an amount of at least about 10% by weight at 20° C.

11. The method according to claim 1, wherein the lignin derivative comprises lignin acetate.

12. The method according to claim 1, wherein the agricultural active is one that is soluble in water at 20° C. in an amount of less than about 2% by weight and is soluble in the organic solvent in an amount of at least about 1% by weight.

13. The method according to claim 12, wherein the agricultural active is one that is soluble in water at 20° C. in an amount of less than about 2% by weight and is soluble in the organic solvent in an amount of at least about 5% by weight.

14. The method according to claim 12, wherein the agricultural active comprises a material selected from the group consisting of pesticides, herbicides and growth regulators.

15. The method according to claim 14, wherein the agricultural active comprises a compound that is selected from the group consisting of acylalanines, alkanamides, amidines, anilides, anilinopyrimidines, aromatic hydrocarbons, chlorophenyls, arylaminopropionic acids, aryloxyalkanoic acids, aryloxyalkanoic acids, aryloxyphenoxypropionates, auxins, avermectins, benzamides, benzenecarboxilic acids, benzilates, benzimidazoles, benzofurans, benzoic acids, benzonitriles, benzothiadiazinones, benzothiazolones, benzotriazines, benzoylureas, bipyridyliums, bis-carbamates, butyrolactones, carbamates, carbamoyltriazoles, chloroacetamides, chloronitriles, chloronicotinyls, cinnamic acids, coumarin anticoagulants, cyclodiene organochlorines, cyclohexanedione oximes, cytokinins, diacylhydrazines, dicarboximides, 2-dimethylaminopropane-1,3-dithiols, dimethyldithiocarbamates, dinitroanilines, dinitrophenols, diphenyl ethers, dithiocarbamates, DMI:imidazoles, DMI: pyridines, DMI:pyrimidines, DMI:triazoles, gibberellins, guanidines, halogenated alkanoic acids, hydroxyanilides, hydroxylbenzonitriles, imidazoles, imidazolinones, indandione anticoagulants, isoxazoles, isoxazolidinones, juvenile hormone mimics, MBI:dehydrases, morpholines, alkylenebis(dithiocarbamates), chloronitriles, dimethyldithiocarbamates, guanidines, inorganics, phenylphridinamines, phosphonates, phthalimides, quinones, sulphamides, natural pyrethrins, neonicotinoids, nitromethylene: neocorticoids, non-ester pyrethroids, N-phenyl carbamates, N-phenylphthalimides, organoarsenics, organochlorines, organophosphorous compounds, organotins, oxadiazines, oxadiazoles, oxathlins, oxozolidinediones, oxazolidinones, oxime carbamates, oxyacetamides, phanylamide: acylalanines, phenylamide: butyrolactones, phenylamide: oxazolidinones, phenylpyrazole herbicides, phenypyrazole insecticides, phenylpyridazines, phenylpyridinamines, phenylpyrroles, phenylureas, pheromones, phosphinic acids, phosphonates, phosphoroamidates, phosphorodithioates, phosphorothiolates, phthalamates, phthalimides, piperazines, polyoxins, pyrazoles, pyrazoliums, pyrethrins, pyrethroids, pyrethroid non-esters, pyridazinones, pyridazinones, pyridazinone analogues, pyridines, pyridinecarboxamides, pyridinecarboxylic acids, pyrimidindiones, pyrimidines, pyrimidinols, pyrimidinyl carbinols, pyrimidinyloxybenzoic compounds, pyrimidinyloxybenzoic analogues, quaternary ammonium compounds, quinolines, quinolinecarboxylic acids, quinones, semi-carbazones, strobilurin compounds, sulfonylaminocarbonyltriazolinones, sulfonylureas, sulfamides, synthetic auxins, tetrazines, tetrazolinones, thiadiazoles, thiocarbamates, 1,3,5-triazines, 1,2,4-triazinones, triazoles, triazolinones, triazolpyrimidines, triketones, uracils, ureas, and mixtures thereof.

16. The method according to claim 15, wherein the agricultural active is a strobilurin compound that is selected from the group consisting metominostrobin, picoxystrobin, famoxadone, azoxystrobin, kresoxim-methyl, trifloxystrobin and mixtures thereof.

17. The method according to claim 14, wherein the agricultural active is a herbicide that is selected from the group consisting of phenoxy acetic acids, 2,4-D, MCPA, phenoxy propionic acids, dichlorprop (2,4-DP), mecoprop (MCPP), phenoxy butyric acids, 2,4-DB, MCPB, benzoic acids, dicamba, picolinic acid compounds, picloram, triclopyr, clopyralid, quinclorac, naptalam, semicarbones, diflufenzopyr-sodium, chloro-s-triazines, atrazine, simazine, cyanazine, methoxy-s-triazines, prometon, methylthio-s-triazines, ametryn, prometryn, hexazinone, metribuzin, substituted ureas, diuron, fluometuron, linuron, tebuthiuron, uracils, bromacil, terbacil, benzothiadiazoles, bentazon, benzonitriles, bromoxymil, phenylcarbamates, desmedipham, phenmedipham, pyridazinones, pyrazon, phenypyriddazines, pyridate, propanil, amitrole, clomazone, fluridone, pyridazinones, norfiurazon, isoxazoles, isoxaflutole, dinitroanilines, benefin, ethalfluralin, oryzalin, pendimethalin, prodiamine, trifluralin, pyridines, dthiopyr, thiazopyr, amides, pronamide, DCPA, carbamothioates (thiocarbamates), EPTC, cycloate, pebulate, triallate, butylate, molinate, thiobencarb, vernolate, seedling root inhibiting amides, napropamide, seedling root inhibiting phenylureas, siduron, bensulfide, chloroacetamides, acetochlor, dimetenamid, propachlor, alachlor, metolachlor, glyphosate, sulfosate, sulfonylureas, bensulfuron, chlorsulfuron, halosulfuron, nicosulfuron, prosulfuron, rimsulfuron, thifensulforon, tribenuron, chiorimuron, ethametsulfuron, metsulfuron, primisulfuron, oxasulfuron, triasulfuron, triflusulfuron, imidazolinones, imazamethabenz, imazamox, imazapic, imazapyr, imazaquin, imazethapyr, aryoxyphenoxyproprionates, diclofop-methyl, fenoxaprop-ethyl, fenoxaprop-p-ethyl, fluazifop-p-butyl, haloxyfop, quizalofop-p-ethyl, cyclohexanediones, clethodim, sethoxydim, tralkoxydim, nitriles, dichiobenil, benzamides, isoxaben, quinclorac, dilute sulfuric acid, monocarbamide dihydrogen sulfate, herbicidal oils, bipyridyliums, diquat, paraquat, diphenylethers, acifluorofen, fomesafen, lactofen, oxyfluorfen, oxidiazoles, fluthiacet, oxadiazon, n-phenylheterocycles, carfentrazone, flumiclorac, sulfentrazone, glufosinate, organic arsenicals, DSMA, MSMA, asulam, endothall, ethofumesate, fosamine, difenzoquat, TCA, and mixtures thereof.

18. The method according to claim 14, wherein the agricultural active is a fungicide that is selected from the group consisting of fludioxonil, fluquinconazole, silthiopham, difenoconazole, a mixture of fludioxonil and fluquinconazole or 4,5-dimethyl-N-2-propenyl-2-(trimethylsilyl)-3-thiophencarboxamid, a mixture of difenoconazole and fluquinconazole or 4,5-dimethyl-N-2-propenyl-2-(trimethylsilyl)-3-thiophencarboxamid, and a mixture of a thienol[2,3-d]pyrimidin-4-one and an azole fungicide, an anilinopyrimidine fungicide, a morpholine fungicide, a strobilurin compound, a pyrrole compound, a phenylamide, a dithiocarbamate fungicide, and mixtures thereof.

19. The method according to claim 14, wherein the agricultural active comprises a compound that is selected from the group consisting of imidacloprid, acetamiprid, thiamethoxam, TI-435 (clothiamidin), simeconazole, fluquinconazole, tebuconazole, silthiopham, terbufos, chlorpyrifos, fipronil, chlorethoxyfos, tefluthrin, fipronil, carbofuran, tebupirimfos, methoprene, hydroprene, and mixtures thereof.

20. The method according to claim 14, wherein the agricultural active comprises one or more compounds selected from the group consisting of imidacloprid, silthiopham, and simeconazole.

21. The method according to claim 20, wherein the agricultural active comprises imidacloprid and silthiopham.

22. The method according to claim 20, wherein the agricultural active comprises imidacloprid and simeconazole.

23. The method according to claim 20, wherein the agricultural active comprises silthiopham and simeconazole.

24. The method according to claim 15, wherein the organic solvent comprises methylene chloride and the lignin derivative comprises lignin acetate.

25. The method according to claim 1, wherein the step of forming an emulsion comprises mixing the aqueous solution and the organic solution under conditions of high shear and thereby forming an oil-in-water emulsion wherein the organic solution forms a discontinuous phase and the aqueous solution forms a continuous phase.

26. The method according to claim 25, wherein the temperature of the aqueous solution and the organic solution is maintained at a level that is no higher than 20° C. below the normal boiling point of the organic solvent during the step comprising forming the emulsion.

27. The method according to claim 26, wherein the temperature of the aqueous solution and the organic solution is maintained at a level that is no higher than 30° C. below the normal boiling point of the organic solvent during the step comprising forming the emulsion.

28. The method according to claim 27, wherein the organic solvent comprises methylene chloride, the agricultural active comprises imidacloprid, the lignin derivative comprises lignin acetate and the temperature is maintained at about 4° C.

29. The method according to claim 25, wherein the organic solution in the discontinuous phase comprises droplets having an average diameter of no larger than about 100 microns.

30. The method according to claim 29, wherein the removing of the organic solvent comprises evaporating the solvent.

31. The method according to claim 29, wherein the microparticles have an average diameter of less than about 100 microns.

32. The method according to claim 31, wherein the microparticles have an average diameter of less than about 25 microns.

33. The method according to claim 32, wherein the microparticles have an average diameter of less than about 10 microns.

* * * * *

UNITED STATES PATENT AND TRADEMARK OFFICE
CERTIFICATE OF CORRECTION

PATENT NO.         : 7,771,749 B2
APPLICATION NO.    : 10/191703
DATED              : August 10, 2010
INVENTOR(S)        : Jawed Asrar et al.

It is certified that error appears in the above-identified patent and that said Letters Patent is hereby corrected as shown below:

On the title page, item [56]: FOREIGN PATENT DOCUMENTS, fifth listed document replace the date "10/2002" with the date -- 12/2006 --.

In Column 20:
Line 10, replace the term "chiorimuron" with the term -- chlorimuron --.
Line 17, replace the term "dichiobenil" with the term -- dichlobenil --.
Line 20, replace the term "acifluorofen" with the term -- aciflurofen --.
Line 35, replace the term "strobilurin" with the term -- strubilurin --.

Signed and Sealed this
Third Day of April, 2012

David J. Kappos
*Director of the United States Patent and Trademark Office*